US008666485B2

(12) United States Patent
Sato et al.

(10) Patent No.: US 8,666,485 B2
(45) Date of Patent: Mar. 4, 2014

(54) BODY COMPOSITION MONITOR CAPABLE OF ACCURATELY MEASURING WHOLE-BODY COMPOSITION AND ACHIEVING FACILITATED MANIPULATION

(75) Inventors: Tetsuya Sato, Nishinomiya (JP); Koichi Tanaka, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 1209 days.

(21) Appl. No.: 12/158,647

(22) PCT Filed: Sep. 19, 2006

(86) PCT No.: PCT/JP2006/318479
§ 371 (c)(1),
(2), (4) Date: Jun. 20, 2008

(87) PCT Pub. No.: WO2007/077650
PCT Pub. Date: Jul. 12, 2007

(65) Prior Publication Data
US 2010/0106045 A1 Apr. 29, 2010

(30) Foreign Application Priority Data
Dec. 28, 2005 (JP) ................................. 2005-379226

(51) Int. Cl.
*A61B 5/05* (2006.01)
(52) U.S. Cl.
USPC ........................................................ 600/547
(58) Field of Classification Search
USPC ........................................................ 600/547
See application file for complete search history.

(56) References Cited

U.S. PATENT DOCUMENTS 6,321,112 B1 * 11/2001 Masuo .......................... 600/547
6,490,481 B1    12/2002 Komatsu et al.
(Continued)

FOREIGN PATENT DOCUMENTS

EP    0 778 001    6/1997
EP    1 386 581    2/2004
(Continued)

OTHER PUBLICATIONS

Cox-Reijven et al. Bio-electrical impedance spectroscopy: Alternatives for the conventional hand-to-foot measurements. Clinical Nutrition (2002); 21(2): 127-133.*
(Continued)

*Primary Examiner* — Brian Szmal
*Assistant Examiner* — Megan Leedy
(74) *Attorney, Agent, or Firm* — Morrison & Foerster LLP

(57) ABSTRACT

A detection portion for detecting a first potential difference between hand and foot by applying a current across the hand and the foot of a subject through both of a hand electrode and a foot electrode and detecting a second potential difference between both hands or between both feet by applying a current across both hands or across both feet of the subject through any one of the hand electrodes and the foot electrodes, a first body composition calculation portion for calculating a first whole-body composition by using whole-body impedance based on a result of detection of the first potential difference, a correction portion for correcting two-limb impedance based on a result of detection of the second potential difference, and a second body composition calculation portion for calculating a second whole-body composition by using the corrected two-limb impedance are included.

31 Claims, 19 Drawing Sheets

(56) References Cited

U.S. PATENT DOCUMENTS

2004/0059242 A1   3/2004  Masuo et al.
2004/0171963 A1*  9/2004  Takehara ............... 600/547
2006/0135885 A1*  6/2006  Iijima et al. ............ 600/547

FOREIGN PATENT DOCUMENTS

| | | |
|---|---|---|
| JP | 57-186124 | 11/1982 |
| JP | 62-169023 | 7/1987 |
| JP | 5-337096 | 12/1993 |
| JP | 10-510455 | 10/1998 |
| JP | 2001-157672 | 6/2001 |
| JP | 2001-286453 | 10/2001 |
| JP | 2004-255120 | 9/2004 |
| JP | 2005-230120 | 9/2005 |
| JP | 2005230120 A * | 9/2005 |
| RU | 2 163 087 | 2/2001 |
| RU | 2 209 582 | 8/2003 |
| WO | WO-97-01303 | 1/1997 |

OTHER PUBLICATIONS

Smye, S.W., et al. (1993). "A comparison of four commercial systems used to measure whole-body electrical impedance," Physiol Meas 14(4):473-8.
Russian Office Action dated Jan. 14, 2010, directed to counterpart Russian Application No. 2008130861/14(038316); 29 pages.
International Search Report mailed Nov. 14, 2006 directed to counterpart International Application No. PCT/JP2006/318479.
Extended European Search Report mailed Jun. 29, 2011, directed to counterpart European Application No. 06798090.4; 6 pages.

* cited by examiner

BODY COMPOSITION MONITOR CAPABLE OF ACCURATELY MEASURING WHOLE-BODY COMPOSITION AND ACHIEVING FACILITATED MANIPULATION

CROSS REFERENCE TO RELATED APPLICATIONS

This application is a national stage application under 35 USC 371 of International Application No. PCT/JP2006/318479, filed Sep. 19, 2006, which claims the benefit of Japanese Patent Application No. 2005-379226, filed Dec. 28, 2005, the entire contents of these applications being hereby incorporated by reference.

TECHNICAL FIELD

The present invention relates to a body composition monitor, and more particularly to a body composition monitor capable of calculating a body composition component (body composition) with a bioelectric impedance method.

BACKGROUND ART

A body composition monitor calculating body composition of a subject using a bioelectric impedance method has conventionally been available. Such a body composition monitor is used for health care management of the subject. The methods of calculating (methods of estimating) the body composition are various, depending on devices.

For example, a method of calculating body composition based on impedance between both hands or both feet is available. Japanese Patent Laying-Open No. 62-169023 (hereinafter Patent Document 1) discloses measurement of weight of adipose tissues in body by measuring impedance between foot and foot or between hand and hand with electrodes brought in contact with the foot or the hand of a subject, for measuring impedance between end portions of the body. In addition, Japanese Patent Laying-Open No. 5-337096 (hereinafter Patent Document 2) discloses the feature that an electrode terminal plate for application and an electrode terminal plate for sensing are provided in two grip portions held by left and right hands, respectively and that a probe measuring body impedance between both hands is included.

In addition, a method of calculating body composition based on impedance of a whole body (between hand and foot) is available. Japanese Patent Laying-Open No. 2001-157672 (hereinafter Patent Document 3) discloses measurement of bio-impedance between an electrode for hand and an electrode for foot in such a manner that electrodes for left foot and right foot for application of a high-frequency signal are electrically connected and electrodes for left foot and right foot for measuring a resistance potential are electrically connected. Japanese National Patent Publication No. 10-510455 (hereinafter Patent Document 4) discloses operation of body composition by measuring impedance for each body part in such a manner that eight electrodes to be brought in contact with a right palm, a right thumb, a left palm, a left thumb, a right front sole, a right rear sole, a left front sole, and a left rear sole respectively are provided and two electrodes to which an alternating current is fed from these electrodes and other two electrodes for measuring a potential difference are selected.

Moreover, as shown in Japanese Patent Laying-Open No. 2005-230120 (hereinafter Patent Document 5), a body composition measurement device having means for switching between an 8-electrode mode (a mode in which eight electrodes brought in contact with both hands and both feet are used) and a 4-electrode mode (a mode in which four electrodes brought in contact with at least one measurement site are used) has also been proposed.

Patent Document 1: Japanese Patent Laying-Open No. 62-169023
Patent Document 2: Japanese Patent Laying-Open No. 5-337096
Patent Document 3: Japanese Patent Laying-Open No. 2001-157672
Patent Document 4: Japanese National Patent Publication No. 10-510455
Patent Document 5: Japanese Patent Laying-Open No. 2005-230120

DISCLOSURE OF THE INVENTION

Problems to be Solved by the Invention

According to Patent Documents 1 and 2, however, only impedance between both feet or between both hands can be measured, and the whole-body composition cannot accurately be measured due to influence of circadian rhythm such as swelling. According to Patent Documents 3 and 4, impedance of the whole body is measured, and therefore the whole-body composition can be measured more accurately than in Patent Documents 1 and 2. The user, however, should bring his/her hands and feet in contact with the electrodes each time the user conducts measurement, and manipulation is bothersome.

In addition, according to Patent Document 5, though a mode can be switched between the 8-electrode mode and the 4-electrode mode, in the 4-electrode mode (in particular in a case of measurement between both feet), influence of circadian rhythm such as swelling is likely and accuracy in measurement of body composition is lower than in the 8-electrode mode. Therefore, if the same subject uses both of these modes, body composition measurement values are inconsistent.

The present invention was made to solve the above-described problems, and an object of the present invention is to provide a body composition monitor capable of accurately measuring whole-body composition and achieving facilitated manipulation.

Means for Solving the Problems

A body composition monitor according to one aspect of the present invention is directed to a body composition monitor for measuring whole-body composition of a subject, including: a plurality of hand electrodes and a plurality of foot electrodes; a detection portion for detecting a first potential difference between a hand and a foot by applying a current across the hand and the foot of the subject through both of the hand electrode and the foot electrode and detecting a second potential difference between both hands or between both feet by applying a current across the both hands or across the both feet of the subject through any one of the hand electrodes and the foot electrodes; a first body composition calculation portion for calculating first whole-body composition using whole-body impedance based on a result of detection of the first potential difference; a correction portion for correcting two-limb impedance based on a result of detection of the second potential difference; and a second body composition calculation portion for calculating second whole-body composition using the two-limb impedance corrected by the correction portion.

The term "whole-body composition" refers at least to fat free mass of the whole body, and more preferably refers to biological information including not only fat free mass but also muscle mass, bone mass, body fat mass, body fat rate, muscle mass rate, visceral fat level, and the like.

The term "two limbs" refers to a pair of limbs out of four limbs (both hands and both feet) and preferably refers any one of both hands and both feet.

Preferably, the first body composition calculation portion calculates the first whole-body composition of the subject based on the whole-body impedance, body information of the subject, and a prescribed first estimation equation showing relation among the whole-body impedance, the body information and the whole-body composition, and the body composition monitor further includes a third body composition calculation portion for calculating third whole-body composition of the subject based on the two-limb impedance based on the second potential difference detected in detection of the first potential difference, the body information of the subject, and a prescribed second estimation equation showing relation among the two-limb impedance, the body information and the whole-body composition, a correction value calculation portion for calculating such a correction value for the two-limb impedance that the first whole-body composition is equal to the third whole-body composition, and a storage portion for storing data of the correction value as correlation information.

The term "correlation information" refers to information for correcting a value relating to two-limb impedance of the subject (two-limb impedance or whole-body composition calculated based on the two-limb impedance).

Preferably, the correction portion corrects the two-limb impedance based on the data of the correction value, and the second body composition calculation portion calculates the second whole-body composition of the subject based on the corrected two-limb impedance, the body information of the subject, and the second estimation equation.

Preferably, the body composition monitor further includes a differential value determination portion for determining whether a differential value between the first whole-body composition and the third whole-body composition is equal to or smaller than a prescribed threshold value, and the correction value calculation portion calculates the correction value when the differential value determination portion determines that the differential value exceeds the threshold value.

Preferably, the body composition monitor further includes a time keeping portion for keeping time and a time zone determination portion for determining a time zone based on data output from the time keeping portion, and the storage portion stores the data of the correction value in association with the time zone in which the detection portion detects the first potential difference.

Alternatively, desirably, the body composition monitor further includes a time keeping portion for keeping time, and the storage portion stores the data of the correction value in association with a time in which the detection portion detects the first potential difference.

Preferably, the correction portion corrects the two-limb impedance based on the data of the correction value corresponding to the time zone in which the detection portion detects the second potential difference.

Preferably, the first body composition calculation portion calculates the first whole-body composition of the subject based on the whole-body impedance, body information of the subject, and a prescribed estimation equation showing relation among the whole-body impedance, the body information and the whole-body composition, and the body composition monitor further includes a correlation calculation portion for calculating correlation between the whole-body impedance and the two-limb impedance based on the second potential difference detected in detection of the first potential difference, and a storage portion for storing correlation data representing correlation as correlation information.

Preferably, the correction portion corrects the two-limb impedance based on the correlation data, and the second body composition calculation portion calculates the second whole-body composition based on the corrected two-limb impedance, the body information of the subject, and the estimation equation.

Preferably, the body composition monitor further includes a time keeping portion for keeping time and a time zone determination portion for determining a time zone based on data output from the time keeping portion, and the storage portion stores the correlation data in association with the time zone when the detection portion detects the first potential difference.

Alternatively, preferably, the body composition monitor further includes a time keeping portion for keeping time, and the storage portion stores the correlation data in association with a time when the detection portion detects the first potential difference.

Preferably, the correction portion corrects the two-limb impedance based on the correlation data corresponding to the time zone when the detection portion detects the second potential difference.

Preferably, a body composition monitor for measuring whole-body composition of a subject includes: a plurality of hand electrodes and a plurality of foot electrodes; a detection portion for detecting a first potential difference between a hand and a foot by applying a current across the hand and the foot of the subject through both of the hand electrode and the foot electrode and detecting a second potential difference between both hands or between both feet by applying a current across the both hands or across the both feet of the subject through any one of the hand electrodes and the foot electrodes; a first body composition calculation portion for calculating first whole-body composition using whole-body impedance based on a result of detection of the first potential difference; a second body composition calculation portion for calculating second whole-body composition using two-limb impedance based on the second potential difference; and a correction portion for correcting the calculated second whole-body composition based on correlation information representing relation between the first whole-body composition and the second whole-body composition.

Preferably, the first body composition calculation portion calculates the first whole-body composition of the subject based on the whole-body impedance, body information of the subject, and a prescribed first estimation equation showing relation among the whole-body impedance, the body information and the whole-body composition, the second body composition calculation portion calculates the second whole-body composition of the subject based on the two-limb impedance, the body information of the subject, and a prescribed second estimation equation showing relation among the two-limb impedance, the body information and the whole-body composition, and the body composition monitor further includes a correlation calculation portion for calculating correlation between the first whole-body composition and the second whole-body composition based on the second potential difference detected in detection of the first potential difference, and a storage portion for storing the correlation data representing correlation as the correlation information.

Preferably, the body composition monitor further includes a time keeping portion for keeping time and a time zone determination portion for determining a time zone based on data output from the time keeping portion, and the storage portion stores the correlation data in association with the time zone in which the detection portion detects the first potential difference.

Alternatively, the body composition monitor further includes a time keeping portion for keeping time, and the storage portion stores the correlation data in association with a time in which the detection portion detects the first potential difference.

Preferably, the correction portion corrects the second whole-body composition based on the correlation data corresponding to the time zone in which the detection portion detects the second potential difference.

Preferably, the body composition monitor further includes a selection portion for selecting execution of any of processing in the first body composition calculation portion and processing in the second body composition calculation portion.

Preferably, the selection portion includes a contact sensing portion for sensing a state of contact of the hand electrode and the foot electrode with a body of the subject, and the selection portion selects execution of processing in the first body composition calculation portion when the contact sensing portion senses contact of both of the hand electrode and the foot electrode with the body and selects execution of processing in the second body composition calculation portion when the contact sensing portion senses contact of any one of the hand electrode and the foot electrode with the body.

Preferably, the body composition monitor further includes: a first unit provided with the hand electrode, the detection portion, the storage portion, the first body composition calculation portion, and the second body composition calculation portion, that can be gripped with both hands of the subject; a second unit provided with the foot electrode, on which both feet of the subject can be placed; and a cable for establishing electrical connection between the first unit and the second unit, the cable being attachable/detachable to/from the first unit or the second unit; the selection portion has a connection sensing portion for sensing whether the cable is connected to the first unit or the second unit, and the selection portion selects execution of processing in the first body composition calculation portion when the connection sensing portion senses connection and selects execution of processing in the second body composition calculation portion for both hands when the connection sensing portion senses absence of connection.

Preferably, the body composition monitor further includes: a first unit provided with the hand electrode, that can be gripped with both hands of the subject; a second unit provided with the foot electrode, on which both feet of the subject can be placed, the second unit including a housing portion for housing the first unit and a housing sensing portion for sensing whether the first unit is housed in the housing portion or not; and a cable for establishing electrical connection between the first unit and the second unit; and the selection portion selects execution of the second body composition calculation portion when the housing sensing portion senses housing and selects execution of processing in the first body composition calculation portion for both feet when the housing sensing portion senses absence of housing.

Preferably, the body composition monitor further includes a determination portion for determining whether the storage portion has stored the correlation information or not when the selection portion selects execution of the second body composition calculation portion, and a notification portion for giving notification to urge the subject of use in a mode corresponding to execution of the processing in the first body composition calculation portion when the determination portion determines that the correlation information has not been stored.

Preferably, the body composition monitor further includes a determination portion for determining whether the storage portion has stored the correlation information or not when the selection portion selects execution of the processing in the second body composition calculation portion, and a notification portion for notifying the subject of prohibition of use in a mode corresponding to execution of the processing in the second body composition calculation portion when the determination portion determines that the correlation information has not been stored.

Preferably, the body composition monitor further includes: a time keeping portion for keeping time and day, the correlation information being stored in the storage portion in association with time and day when the correlation information was set; a determination portion for determining whether a prescribed time period has elapsed since the time and day stored in the storage portion, when the selection portion selects execution of the processing in the second body composition calculation portion; and a notification portion for notifying the subject of prohibition of use in a mode corresponding to execution of the processing in the second body composition calculation portion when the determination portion determines that the time period has elapsed.

Preferably, the body composition monitor further includes a determination portion for determining whether the storage portion has stored the correlation information or not when the selection portion selects execution of the second body composition calculation portion, and a notification portion for notifying that correction processing by the correction portion is not applicable in presenting the calculated second whole-body composition to the subject, when the determination portion determines that the correlation information has not been stored.

Preferably, the body composition monitor further includes: a first unit provided with the hand electrode, that can be gripped with both hands of the subject; a second unit provided with the foot electrode, on which both feet of the subject can be placed, the second unit including a weight measurement portion for measuring weight out of the body information; and a weight storage portion for storing the weight measured by the weight measurement portion, and the second body composition calculation portion calculates the second whole-body composition of the subject by reading the weight stored in the weight storage portion.

Effects of the Invention

According to the present invention, even when the whole-body composition is measured based on the two-limb impedance, the body composition as reliable as in measurement based on the whole-body impedance can be derived.

Figure 1:
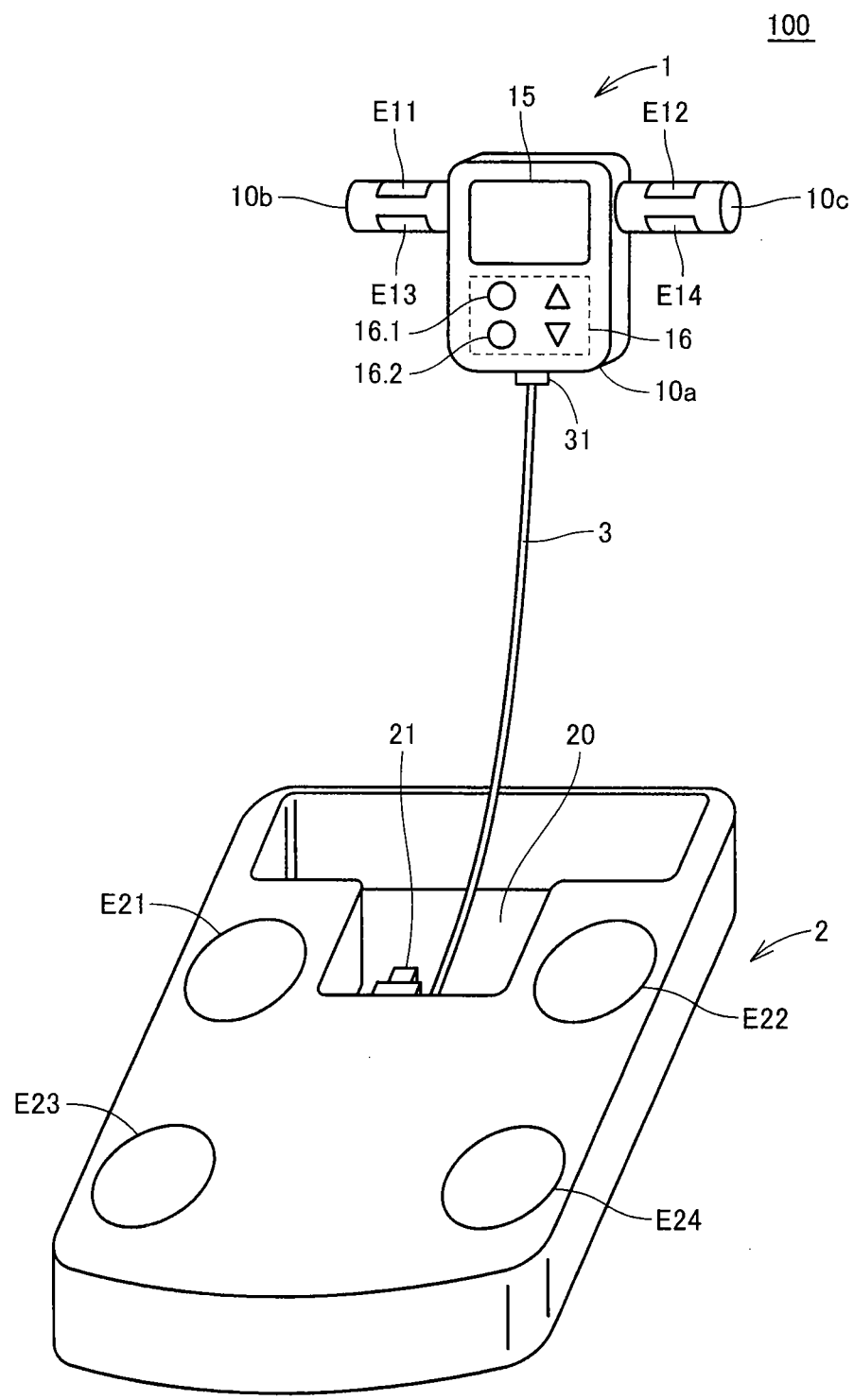
FIG. 1 illustrates exemplary appearance of a body composition monitor in first to third embodiments of the present invention.

DESCRIPTION OF THE REFERENCE SIGNS 1 upper-limb unit; 2 lower-limb unit; 3 cable; 10a main portion; 10b, 10c grip; 11 detection portion; 12, 12A, 12B control portion; 13 timer; 14 memory; 15 display portion; 16 manipulation portion; 17 power supply portion; 18, 31 connector; 19 sensor; housing portion; 21 housing sensing portion; 22 weight measurement portion; 100 body composition monitor; 101 whole-body impedance measurement portion; 102 two-limb impedance measurement portion; 103 first body composition calculation portion; 104, 205, 304 correction portion; 105, 204 second body composition calculation portion; 106 correlation setting portion; 206, 306 correlation calculation portion; 1061 third body composition calculation portion; 1062 correction value calculation portion; E10 hand electrode; E20 foot electrode; and E11, E12, E13, E14, E21, E22, E23, E24 electrode.

BEST MODES FOR CARRYING OUT THE INVENTION

An embodiment of the present invention will be described in detail with reference to the drawings. It is noted that the same or corresponding elements in the drawings have the same reference characters allotted.

First Embodiment

<Appearance and Configuration of Body Composition Monitor in the First Embodiment of the Present Invention>

Referring to FIG. 1, a body composition monitor 100 in the first embodiment of the present invention is constituted of an upper-limb unit 1 that a subject can grip with both hands, a lower-limb unit 2 on which both feet of the subject can be placed, and a cable 3 for electrically connecting upper-limb unit 1 and lower-limb unit 2 to each other.

Upper-limb unit 1 includes a main portion 10a and grips 10b and 10c provided on left and right of main portion 10a respectively. Main portion 10a is provided with a display portion 15 for displaying a measurement result and various types of information and a manipulation portion 16 manipulated by the subject, for accepting an instruction from the subject or an input of various types of information. Grips 10b and 10c are provided with a plurality of electrodes E11, E12, E13, and E14. Grips 10b and 10c are configured to be gripped with both hands of the subject. Electrodes E11 and E13 are provided in grip 10b for left hand, and electrodes E12 and E14 are provided in grip 10c for right hand. Electrodes E11 and E12 provided on the upper side (on a side of the head of the subject in a posture for measurement) of grips 10b and 10c respectively are electrodes for applying a current, while electrodes E13 and E14 provided on the lower side of grips 10b and 10c respectively are electrodes for sensing a voltage. Here, though upper-limb unit 1 is described assuming that it includes grips 10b and 10c formed like a handle, the grip is not limited as such. The subject should only be able to grip upper-limb unit 1 with both hands and electrodes E11 to E14 should only be arranged in portions gripped with both hands. In other words, electrodes E11 and E13 should only be in contact with the left hand of the subject and electrodes E12 and E14 should only be in contact with the right hand thereof.

A plurality of electrodes E21, E22, E23, and E24 are provided on the upper surface of lower-limb unit 2 (surface on which both feet of the subject are placed). Among these electrodes, electrodes E21 and E22 provided on a front side (a toe side of the subject in a posture for measurement) of lower-limb unit 2 are electrodes for applying a current, while electrodes E23 and E24 provided on a rear side (a heel side of the subject in a posture for measurement) of lower-limb unit 2 are electrodes for sensing a voltage. In addition, lower-limb unit 2 includes a housing portion 20 for housing upper-limb unit 1. Moreover, lower-limb unit 2 is preferably provided with a housing sensing portion 21 for sensing housing of upper-limb unit 1 in housing portion 20. Housing sensing portion 21 is implemented, for example, by a sensor.

A connector 31 for allowing attachment to a connector 18 contained in upper-limb unit 1 is preferably provided at an end portion of cable 3. In the present embodiment, upper-limb unit 1 and cable 3 can be attached to/detached from each other, however, lower-limb unit 2 and cable 3 may be attached to/detached from each other.

In the description below, electrodes E11 to E14 are collectively referred to as "hand electrode E10" and electrodes E21 to E24 are collectively referred to as "foot electrode E20."

Figure 2:
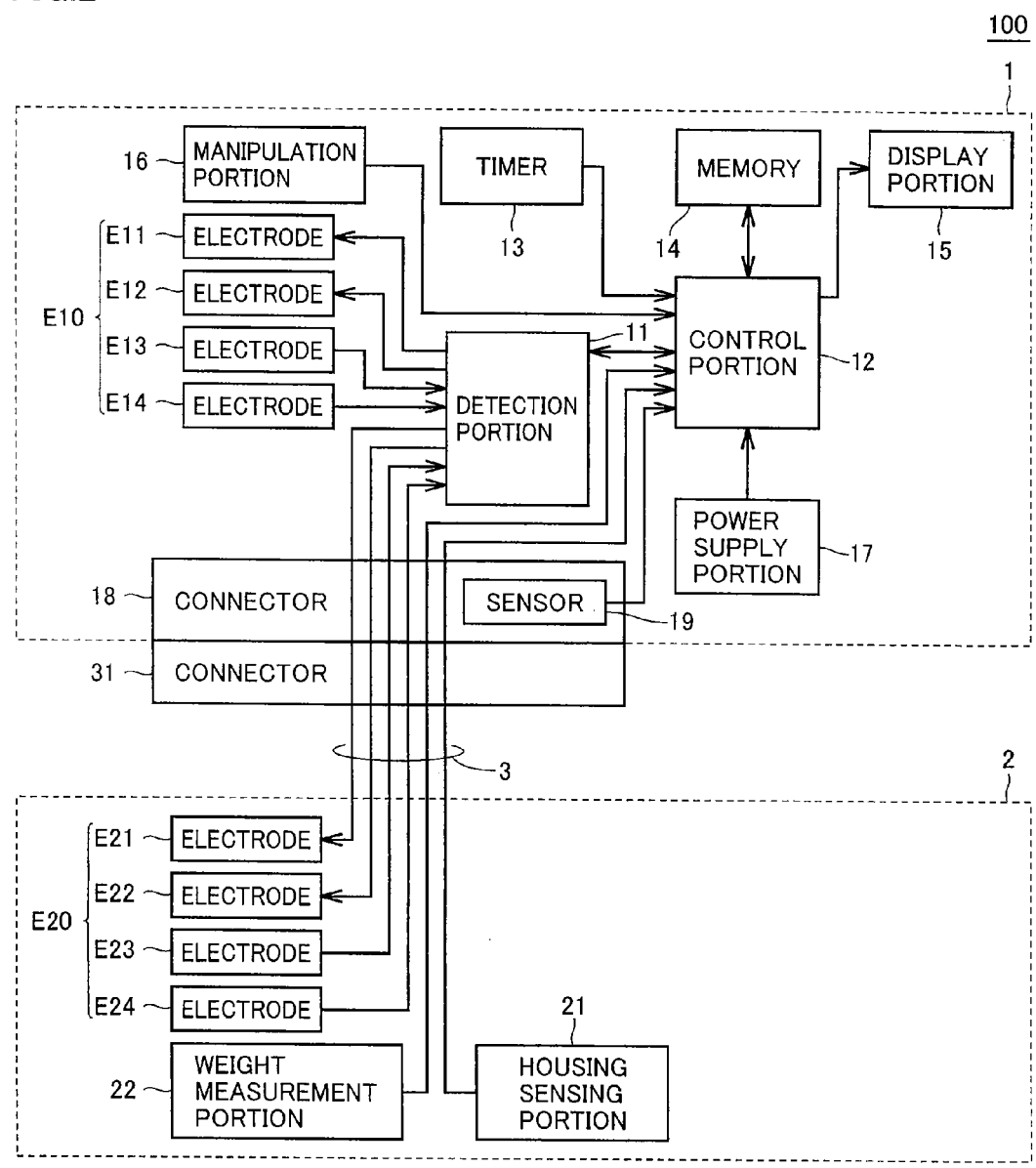
FIG. 2 is a block diagram showing a hardware configuration of the body composition monitor in the first to third embodiments of the present invention.

Referring to FIG. 2 for a hardware configuration of body composition monitor 100 in the first embodiment of the present invention, in addition to hand electrode E10, display portion 15, manipulation portion 16, and connector 18 described above, upper-limb unit 1 further includes a detection portion 11 for detecting a potential difference between a hand and a foot (whole body) by applying a current across the hand and the foot of the subject through both of hand electrode E10 and foot electrode E20 and detecting a potential difference between both hands or between both feet by applying a current across both hands or across both feet of the subject through any one of hand electrode E10 and foot electrode E20, a control portion 12 for controlling entire body composition monitor 100, a timer 13 for keeping time and day, a memory 14 for storing various types of data and programs, a power supply portion 17 for supplying electric power to control portion 12, and a sensor 19 for sensing attachment and detachment of cable 3 and upper-limb unit 1 to/from each other.

Detection portion 11 switches between electrodes under control of control portion 12. In addition, information on the detected potential difference is output to control portion 12. For example, detection portion 11 has a switch (not shown) connected to all hand electrodes E10 and foot electrodes E20, for switching between electrodes in accordance with an instruction from control portion 12, and a constant current generation portion (not shown) for feeding a constant current to at least one pair of electrodes for current selected by the switch, and detects a potential difference between at least one pair of electrodes for voltage selected by the switch while the constant current is applied to the subject through the electrodes for current.

In the description below, impedance based on a potential difference detected by detection portion 11 with both of hand electrode E10 and foot electrode E20 is referred to as "whole-body impedance". In addition, impedance based on a potential difference detected by detection portion 11 with only hand electrode E10 is referred to as "both-hand impedance" and impedance based on a potential difference detected by detection portion 11 with only foot electrode E20 is referred to as "both-feet impedance." Further, the both-hand impedance and/or the both-feet impedance are/is also referred to as "two-limb impedance."

Control portion 12 is implemented, for example, by a CPU (Central Processing Unit). Memory 14 is implemented by a non-volatile memory such as a flash memory. Display portion 15 is implemented, for example, by liquid crystals. Manipulation portion 16 includes a power switch 16.1 for input of an instruction of ON/OFF of power, a measurement start switch 16.2 for giving an instruction to start measurement, and the like.

Lower-limb unit 2 desirably further includes a weight measurement portion 22 for measuring weight of the subject, in addition to foot electrode E20 and housing sensing portion 21 described above. Weight measurement portion 22 is implemented, for example, by a sensor.

Body composition monitor 100 in the present embodiment is an apparatus for measuring whole-body composition of the subject. Body composition monitor 100 has a "whole-body measurement mode" for measuring the whole-body composition based on the whole-body impedance (denoted as "Zw") and a "simplified measurement mode" for measuring the whole-body composition based on the two-limb impedance, namely, the both-hand impedance (denoted as "Zh") or the both-feet impedance (denoted as "Zf"). The simplified measurement mode includes a "hand-simplified measurement mode" for measuring the whole-body composition based on both-hand impedance Zh and a "foot-simplified measurement mode" for measuring the whole-body composition based on both-feet impedance Zf.

The measurement posture of the subject when the whole-body composition is measured in the whole-body measurement mode is such that both hands and both feet of the subject are in contact with hand electrode E10 and foot electrode E20 respectively. The measurement posture of the subject when the whole-body composition is measured in the hand-simplified measurement mode is such that both hands of the subject are in contact with hand electrode E10. The measurement posture of the subject when the whole-body composition is measured in the foot-simplified measurement mode is such that both feet of the subject are in contact with foot electrode E20.

Figure 3:
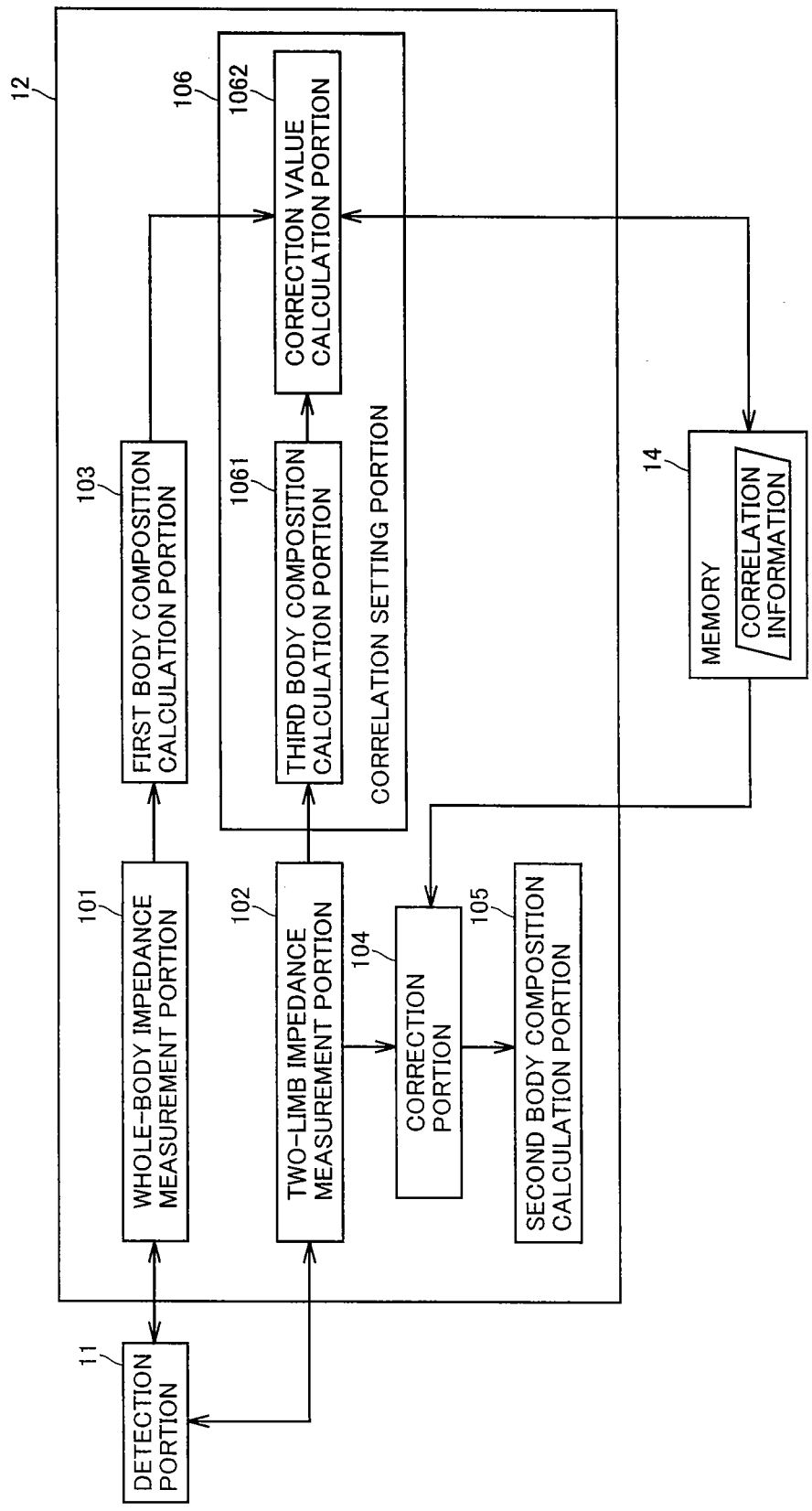
FIG. 3 is a functional block diagram of the body composition monitor in the first embodiment of the present invention.

Referring to FIG. 3 showing a functional block diagram of body composition monitor 100 in the first embodiment of the present invention, control portion 12 includes a whole-body impedance measurement portion 101 for measuring whole-body impedance, a two-limb impedance measurement portion 102 for measuring two-limb impedance, a first body composition calculation portion 103 for calculating the whole-body composition based on the whole-body impedance measured by whole-body impedance measurement portion 101, a correction portion 104 for correcting the two-limb impedance measured by two-limb impedance measurement portion 102, a second body composition calculation portion 105 for calculating the whole-body composition based on the two-limb impedance corrected by correction portion 104, and a correlation setting portion 106 for setting correlation information.

The correlation information refers to data of a correction value for the two-limb impedance in the first embodiment of the present invention.

Whole-body impedance measurement portion 101 measures the whole-body impedance by controlling detection portion 11 in the whole-body measurement mode. Specifically, whole-body impedance measurement portion 101 carries out control for detecting a potential difference between electrodes E13, E14 and electrodes E23, E24 (hereinafter referred to as "whole-body potential difference") while a current flows from electrodes E11 and E12 to electrodes E21 and E22 so that the current is applied to the whole body of the subject. Whole-body impedance Zw is calculated (measured) based on the whole-body potential difference thus detected. In measuring the whole-body impedance, electrode E11 and electrode E12, electrode E21 and electrode E22, electrode E13 and electrode E14, and electrode E23 and electrode E24 are preferably short-circuited, respectively.

Two-limb impedance measurement portion 102 measures the two-limb impedance by controlling detection portion 11 in each of the whole-body measurement mode and the simplified measurement mode. In the whole-body measurement mode, both of both-hand impedance Zh and both-feet impedance Zf are measured. In the hand-simplified measurement mode, both-hand impedance Zh is measured, and in the foot-simplified measurement mode, both-feet impedance Zf is measured. In measuring both-hand impedance Zh, specifically, two-limb impedance measurement portion 102 carries out control for detecting a potential difference between electrodes E13 and E14 (hereinafter referred to as "both-hand potential difference") while a current flows between electrodes E11 and E12 so that the current is applied across both hands of the subject. In measuring both-feet impedance Zf, specifically, two-limb impedance measurement portion 102 carries out control for detecting a potential difference between electrode E23 and electrode E24 (hereinafter referred to as "both-feet potential difference") while a current flows between electrode E21 and electrode E22 so that the current is applied across both feet of the subject.

Each of first body composition calculation portion 103 and second body composition calculation portion 105 calculates, for example, a body fat rate as the whole-body composition. The body fat rate (% FAT) is calculated by using an equation as follows:

$$\% \text{ FAT} = W - FFM/W \times 100 \quad (1)$$

(where FFM represents fat free mass and W represents weight.)

Here, an equation for estimating fat free mass FFM (of the whole body) is set in advance for each of an example where whole-body impedance Zw is used, an example where both-hand impedance Zh is used, and an example where both-feet impedance Zf is used. Namely, the fat free mass of the subject is calculated by using the following estimation equation predetermined based on correlation with a reference measured for example with MRI, that represents relation among each impedance, the body information, and the fat free mass. It is noted that the fat free mass estimated by using whole-body impedance Zw, the fat free mass estimated by using both-hand impedance Zh, and the fat free mass estimated by using both-feet impedance Zf are denoted as "FFM_w", "FFM_h" and "FFM_f", respectively.

$$FFM\_w = \alpha_1 \cdot H^2/Zw + \beta_1 \cdot W + \gamma_1 \quad (2)$$

$$FFM\_h = \alpha_2 \cdot H^2/Zh + \beta_2 \cdot W + \gamma_2 \quad (3)$$

$$FFM\_f = \alpha_3 \cdot H^2/Zf + \beta_3 \cdot W + \gamma_3 \quad (4)$$

(where $\alpha_1$, $\beta_1$, $\gamma_1$, $\alpha_2$, $\beta_2$, $\gamma_2$, $\alpha_3$, $\beta_3$, and $\gamma_3$ represent coefficients, H represents height, and W represents weight.)

The coefficient in the estimation equation above may be different depending on an attribute (age or sex) of an individual.

From the foregoing, first body composition calculation portion 103 calculates the whole-body composition (body fat rate) of the subject based on whole-body impedance Zw measured by whole-body impedance measurement portion 101, the body information of the subject, and equations (1) and (2) above. In addition, in the hand-simplified measurement mode, second body composition calculation portion 105 calculates the whole-body composition of the subject based on the both-hand impedance (denoted as "Zh'") corrected by correction portion 104, the body information of the subject, and equations (1) and (3) above. Moreover, in the foot-simplified measurement mode, second body composition calculation portion 105 calculates the whole-body composition of the subject based on the both-feet impedance (denoted as "Zf'") corrected by correction portion 104, the body information of the subject, and equations (1) and (4) above. In the present embodiment, as shown in estimation equations (2) to (4), the whole-body composition is calculated based on each impedance value and the body information, however, the whole-body composition may be calculated based on a value of each potential difference and the body information.

In the simplified measurement mode, correction portion 104 corrects the two-limb impedance measured by two-limb impedance measurement portion 102 based on the correlation information stored in memory 14 (data of the correction value for the two-limb impedance).

Correlation setting portion 106 has a third body composition calculation portion 1061 for calculating the whole-body composition based on the two-limb impedance measured by two-limb impedance measurement portion 102 in the whole-body measurement mode, and a correction value calculation portion 1062 for calculating such a correction value for the two-limb impedance that the whole-body composition calculated by first body composition calculation portion 103 is equal to the whole-body composition calculated by third body composition calculation portion 1061. Specifically, third body composition calculation portion 1061 calculates the whole-body composition of the subject based on both-hand impedance Zh based on the both-hand potential difference detected in detection of the whole-body potential difference, the body information of the subject, and equations (1) and (3) above. In addition, third body composition calculation portion 1061 calculates the whole-body composition of the subject based on both-feet impedance Zf based on the both-feet potential difference detected in detection of the whole-body potential difference, the body information of the subject, and equations (1) and (4) above. Here, "in detection of the whole-body potential difference (in which the whole-body potential difference is detected)" should only be at least within a period of a series of measurement processes in the whole-body measurement mode.

Control portion 12 preferably further selects execution of any of the whole-body measurement mode and the simplified measurement mode, that is, execution of body composition calculation by using first body composition calculation portion 103 or execution of body composition calculation by using second body composition calculation portion 105. Here, control portion 12 more preferably selects any measurement mode from among the whole-body measurement mode, the hand-simplified measurement mode and the foot-simplified measurement mode. A specific selection method will be described later.

In addition, control portion 12 preferably determines a time zone (such as a morning time zone, a day time zone, a night time zone, and the like) in detecting each potential difference. Specifically, in the whole-body measurement mode, the time zone in which the whole-body potential difference is detected is determined based on the time keeping data from timer 13. Alternatively, in the simplified measurement mode, the time zone in which both-hand potential difference or both-feet potential difference is detected is determined based on the time keeping data from timer 13. Here, "in which both-hand potential difference or both-feet potential difference is detected" should only be at least within a period of a series of measurement processes in the simplified measurement mode.

An operation in each functional block may be implemented by executing software stored in memory 14 or may at least partially be implemented by hardware.

Figure 4:
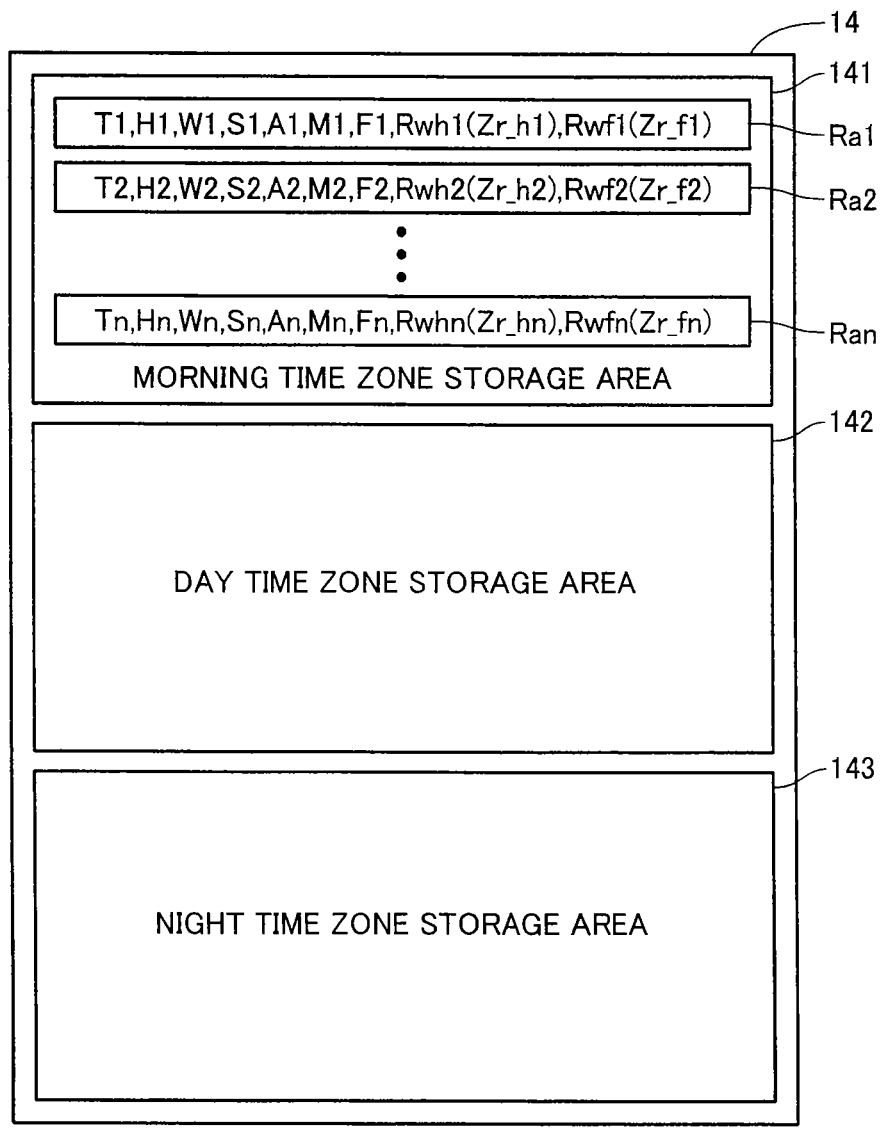
FIG. 4 illustrates an exemplary data structure in a memory of the body composition monitor in the first embodiment of the present invention.

Referring to FIG. 4, memory 14 in body composition monitor 100 in the first embodiment of the present invention includes a morning time zone storage area 141 for storing a measurement result in a morning time zone, a day time zone storage area 142 for storing a measurement result in a day time zone, and a night time zone storage area 143 for storing a measurement result in a night time zone. In which area among these storage areas the measurement result is to be stored is determined depending on the time zone selected by control portion 12. A range of the time zone may be defined in advance at the time of shipment, or it may be set in accordance with a cycle of life of a user himself/herself. For example, a period from 5 o'clock to 10 o'clock, a period from 10 o'clock to 16 o'clock, and a period from 16 o'clock to 4 o'clock of the next day may be defined as the "morning time zone," the "day time zone" and the "night time zone," respectively.

When the body composition measurement processing which will be described in detail later is performed, the measurement result is stored in a unit of a record Ra in a storage area of memory 14, in accordance with the time zone of measurement. Record Ra (Ra1, Ra2, . . . , Ran) includes time and day data T of measurement (in detection of each potential difference), height input value data H serving as the body information, weight value data W serving as the body information, sex data S serving as the body information, age data A serving as the body information, measurement mode data M, whole-body composition data F serving as the measurement result, correlation information Rwh, and correlation information Rwf. These types of data should only be stored in each area in association with each other for each measurement, and a manner of storage is not limited to the manner using record Ra. In addition, though the storage area is provided in advance for each time zone here, the storage area for each time zone may not be provided. For example, identification data indicating a time zone may be included in record Ra and records may be stored in memory 14 in the order of time and day of measurement.

Measurement mode data M is identification information indicating which measurement mode out of the whole-body measurement mode, the hand-simplified measurement mode and the foot-simplified measurement mode was carried out. In other words, measurement mode data M is information indicating whether the body composition was calculated by first body composition calculation portion 103 or by second body composition calculation portion 105. For example, if the body composition was calculated in the whole-body measurement mode, "0" is stored; if the body composition was calculated in the hand-simplified measurement mode, "1" is stored; and if the body composition was calculated in the foot-simplified measurement mode, "2" is stored.

Whole-body composition data F shows the final body composition measurement result, and it is data of the body fat rate calculated by first body composition calculation portion 103 or second body composition calculation portion 105.

In the present embodiment, data of a correction value Zr_h for both-hand impedance Zh is stored as correlation information Rwh.

In the present embodiment, data of a correction value Zr_f for both-feet impedance Zf is stored as correlation information Rwf.

When the whole-body composition is measured in the whole-body measurement mode, all the data above is stored in memory 14. On the other hand, when the whole-body composition is measured in the hand-simplified measurement mode, data other than weight W, correlation information Rwh and correlation information Rwf is stored in memory 14. Alternatively, when the whole-body composition is measured in the foot-simplified measurement mode, data other than correlation information Rwh and correlation information Rwf is stored in memory 14.

<Operation of Body Composition Monitor in the First Embodiment of the Present Invention>

Figure 5:
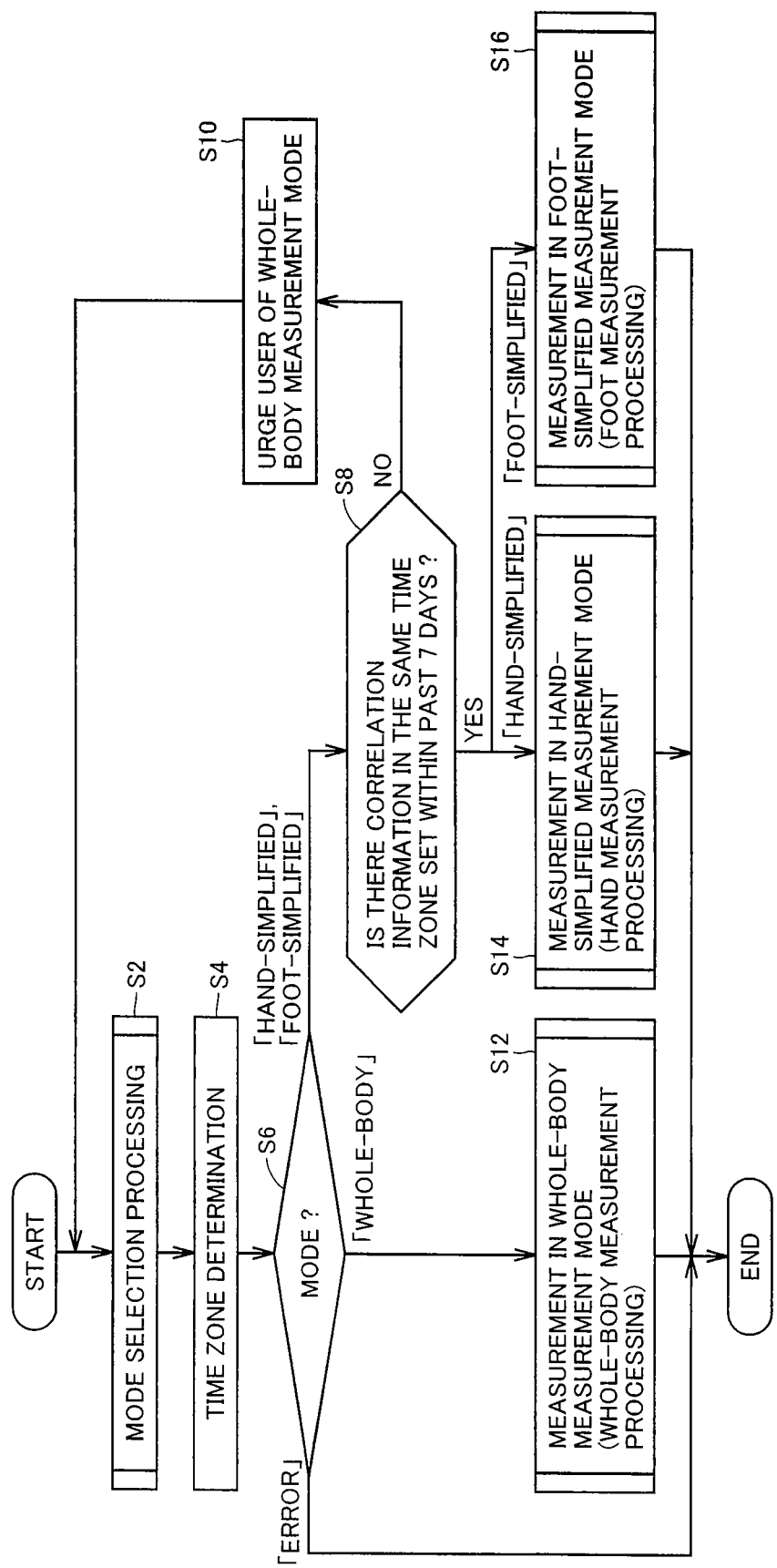
FIG. 5 is a flowchart showing processing for measuring body composition performed by a control portion of the body composition monitor in the first to third embodiments of the present invention.

The body composition measurement processing performed by control portion 12 in body composition monitor 100 in the first embodiment of the present invention, shown in the flowchart in FIG. 5, is stored in advance in memory 14 as a program, and a function of the body composition measurement processing is achieved by reading and execution of the program by control portion 12.

Referring to FIG. 5, control portion 12 performs mode selection processing (step S2). A sub routine of the mode selection processing in step S2 is shown in FIG. 6.

Figure 6:
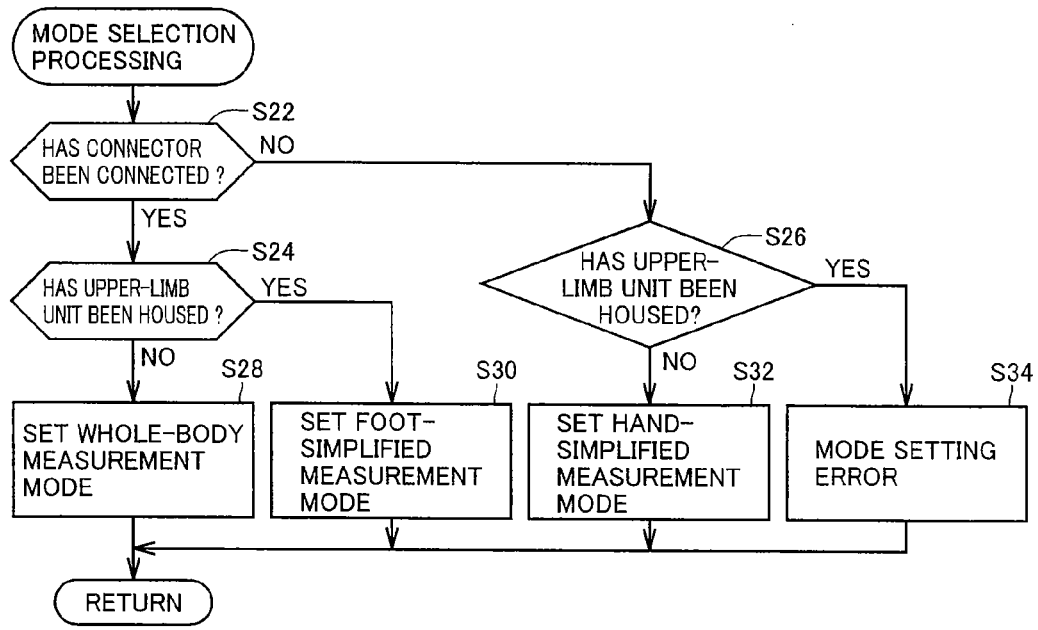
FIG. 6 is a flowchart showing processing for selecting a mode in the first to third embodiments of the present invention.

Referring to FIG. 6, control portion 12 determines whether connector 18 and connector 31 are connected to each other or not, based on a signal from sensor 19 (step S22). Namely, whether upper-limb unit 1 and cable 3 are connected to each other or not is determined. If it is determined that connector 18 and connector 31 are connected to each other (YES in step S22), the process proceeds to step S24. On the other hand, if it is determined that connector 18 and connector 31 are not connected to each other (NO in step S22), the process proceeds to step S26.

In step S24, control portion 12 determines whether upper-limb unit 1 has been housed in housing portion 20 or not, based on a signal from housing sensing portion 21. If it is determined that upper-limb unit 1 is not housed in housing portion 20 (NO in step S24), control portion 12 selects the whole-body measurement mode and sets subsequent measurement processing to the whole-body measurement mode (step S28). If it is determined that upper-limb unit 1 has been housed in housing portion 20 (YES in step S24), the foot-simplified measurement selected is made and subsequent measurement processing is set to the foot-simplified measurement mode (step S30).

In step S26 as well, control portion 12 determines whether upper-limb unit 1 is housed in housing portion 20 or not, based on the signal from housing sensing portion 21. If it is determined that upper-limb unit 1 is not housed in housing portion 20 (NO in step S26), control portion 12 selects the hand-simplified measurement mode and sets subsequent measurement processing to the hand-simplified measurement mode (step S32). On the other hand, if it is determined that upper-limb unit 1 has been housed in housing portion 20 (YES in step S26), decision as mode setting error is made (step S34). The mode selection processing thus ends.

As the measurement mode is thus automatically selected, measurement in accordance with each mode is started when the subject simply takes the measurement posture in each measurement mode.

Referring again to FIG. 5, control portion 12 determines the time zone of measurement based on data output from timer 13 (step S4).

Thereafter, control portion 12 selects the mode selected in step S2 (step S6). If the whole-body measurement mode has been set, measurement processing in the whole-body measurement mode (whole-body measurement processing) is performed (step S12). If the hand-simplified measurement mode or the foot-simplified measurement mode has been set, control portion 12 determines whether or not there is correlation information in the same time zone, that was set in the past, for example, within seven days (step S8). If it is determined that there is correlation information in the same time zone set within the past seven days (YES in step S8), the process proceeds to step S14 or step S16. Namely, if the mode selected in step S2 is the hand-simplified measurement mode, the process proceeds to step S14. If the mode selected in step S2 is the foot-simplified measurement mode, the process proceeds to step S16. In the present embodiment, "the same time zone" refers to the time zone the same as the time zone determined in step S4 (that is, the time zone of present measurement).

In step S14, the measurement processing in the hand-simplified measurement mode (hand measurement processing) is performed. In step S16, the measurement processing in the foot-simplified measurement mode (foot measurement processing) is performed.

If it is determined in step S8 above that there is no correlation information in the same time zone set within the past seven days (NO in step S8), control portion 12 urges the user to conduct measurement in the whole-body measurement mode (step S10). Specifically, for example, processing for displaying a message that "conduct measurement in the whole-body measurement mode" on display portion 15 is performed.

In the description above, the mode is selection based on signals from sensor 19 and housing sensing portion 21, however, the selection method is not limited as such. For example, a button corresponding to each mode may be provided in manipulation portion 16, so that the subject can select which mode to carry out. Alternatively, the mode selection processing as shown in FIG. 7 may be performed.

Figure 7:
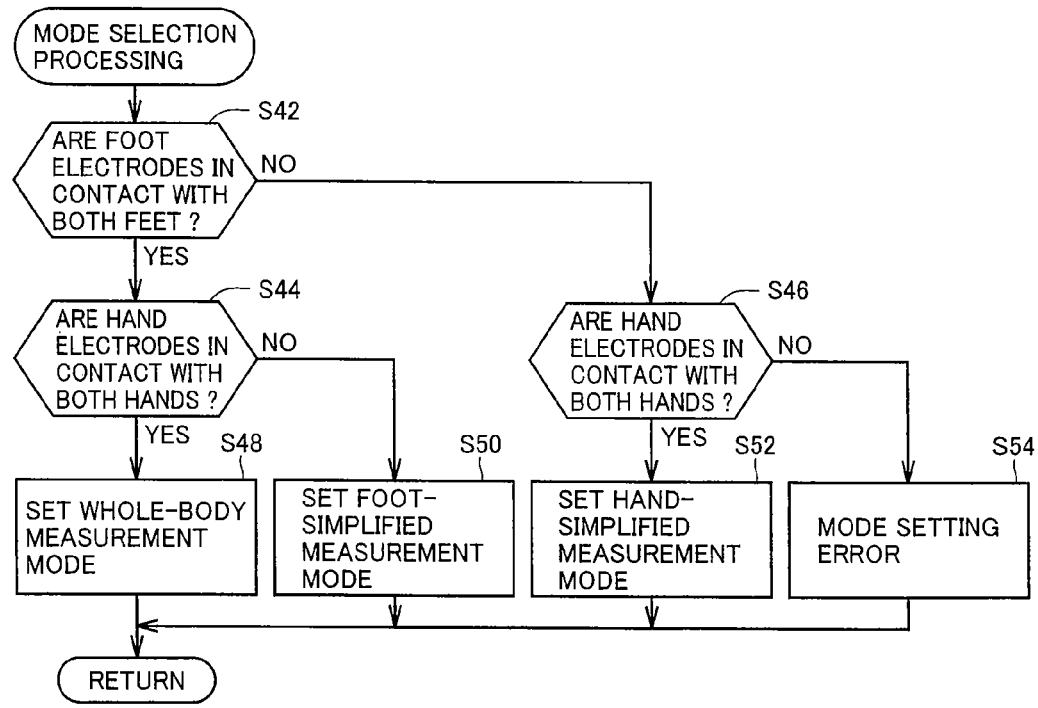
FIG. 7 is a flowchart showing another example of processing for selecting a mode in the first to third embodiments of the present invention.

Referring to FIG. 7, control portion 12 determines whether or not foot electrodes E20 are in contact with both feet of the subject (step S42). If it is determined that foot electrodes E20 are in contact with both feet of the subject (YES in step S42), the process proceeds to step S44.

On the other hand, if it is determined that foot electrodes E20 are in contact with neither of the feet of the subject (NO in step S42), the process proceeds to step S46.

In step S44, control portion 12 determines whether hand electrodes E10 are in contact with both hands of the subject. If it is determined that hand electrodes E10 are in contact with both hands of the subject (YES in step S44), subsequent measurement processing is set to the whole-body measurement mode (step S48). If it is determined that hand electrodes E10 are in contact with neither of the hands (NO in step S44), subsequent measurement processing is set to the foot-simplified measurement mode (step S50).

In step S46, whether or not hand electrodes E10 are in contact with both hands of the subject is determined. If it is determined that hand electrodes E10 are in contact with both hands of the subject (YES in step S46), the hand-simplified measurement mode is set (step S52). On the other hand, if it is determined that hand electrodes E10 are in contact with neither of the hands of the subject (NO in step S46), decision as mode setting error is made (step S54). The mode selection processing thus ends.

Determination in steps S42, 44 and 46 can be made by using, for example, a method disclosed in Patent Document 5. More specifically, determination of a contact state can be made by comparing impedance based on a potential difference in each body part (whole-body, both hands, and both feet) with a reference range predetermined for each body part.

Each of the whole-body measurement processing (S12), the hand measurement processing (S14) and the foot measurement processing (S16) shown in FIG. 5 will be described with reference to the sub routine.

Figure 8:
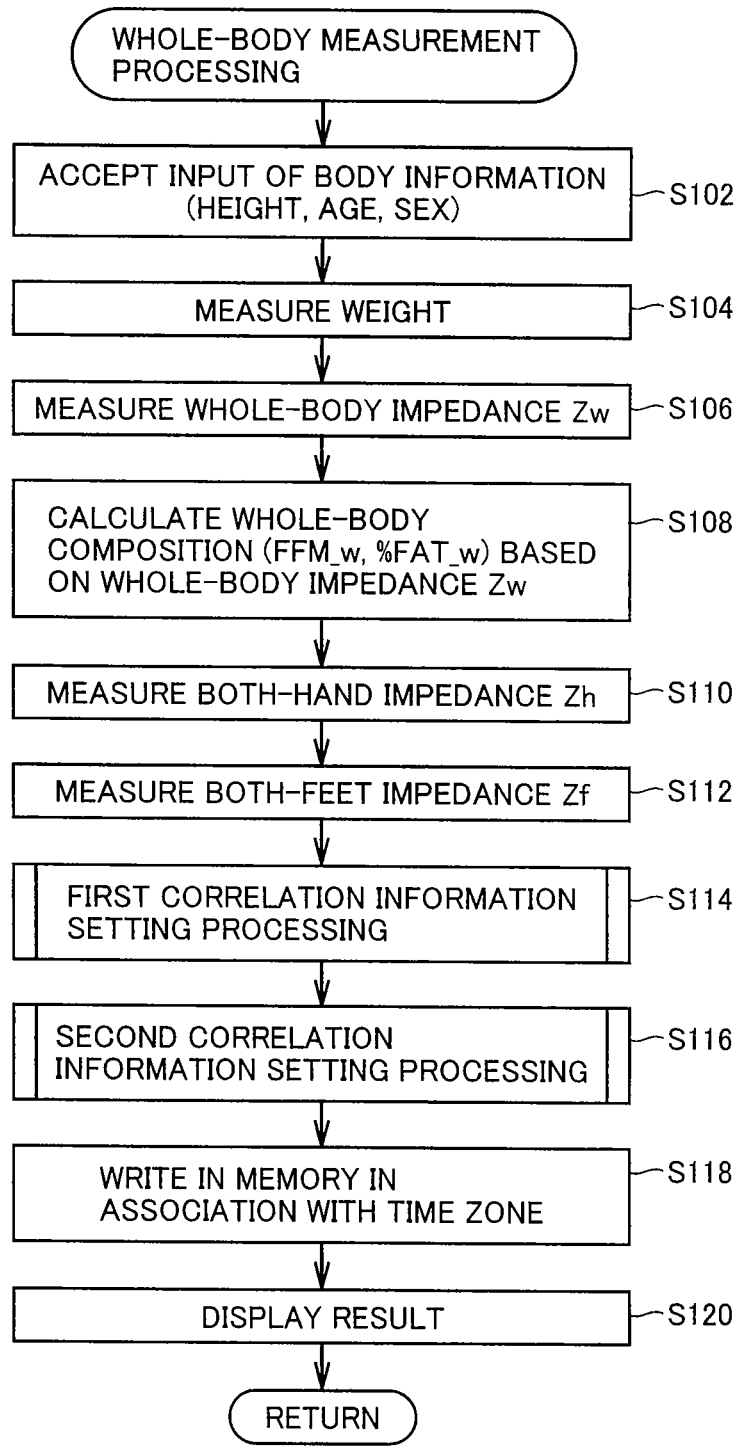
FIG. 8 is a flowchart showing whole-body measurement processing in the first to third embodiments of the present invention.

Referring to FIG. 8 for the whole-body measurement processing in the first embodiment of the present invention, control portion 12 accepts input of the body information (height, age, sex) from the subject (step S102). Thereafter, control portion 12 measures weight with weight measurement portion 22 (step S104).

Thereafter, whole-body impedance measurement portion 101 measures whole-body impedance Zw of the subject (step S106). In succession, first body composition calculation portion 103 calculates the whole-body composition, that is, the body fat rate (denoted as "% FAT_w") based on whole-body impedance Zw measured in step S106. More specifically, initially, whole-body fat free mass (FFM_w) is calculated by using whole-body impedance Zw, the body information of the subject, and estimation equation (2). Thereafter, the body fat rate (% FAT_w) is calculated by using equation (1). In the present embodiment, the body fat rate is calculated after the fat free mass is calculated, however, the body fat rate may be calculated directly based on whole-body impedance Zw and the body information of the subject. Alternatively, only the fat free mass may be calculated.

Thereafter, two-limb impedance measurement portion 102 measures both-hand impedance Zh of the subject (step S110), and in addition, measures both-feet impedance Zf of the subject (S112). Thereafter, correlation setting portion 106 performs first correlation information setting processing (step S114) and second correlation information setting processing (step S116). Details of the setting processing will be described later.

In succession, control portion 12 writes the measurement result, the correlation information or the like in memory 14 in association with the time zone determined in step S4 (step S118), and causes display portion 15 to display the measurement result (body fat rate) (step S 120). The whole-body measurement processing thus ends.

Here, the first correlation information setting processing (S114) and the second correlation information setting processing (S116) will be described in detail.

Figure 9:
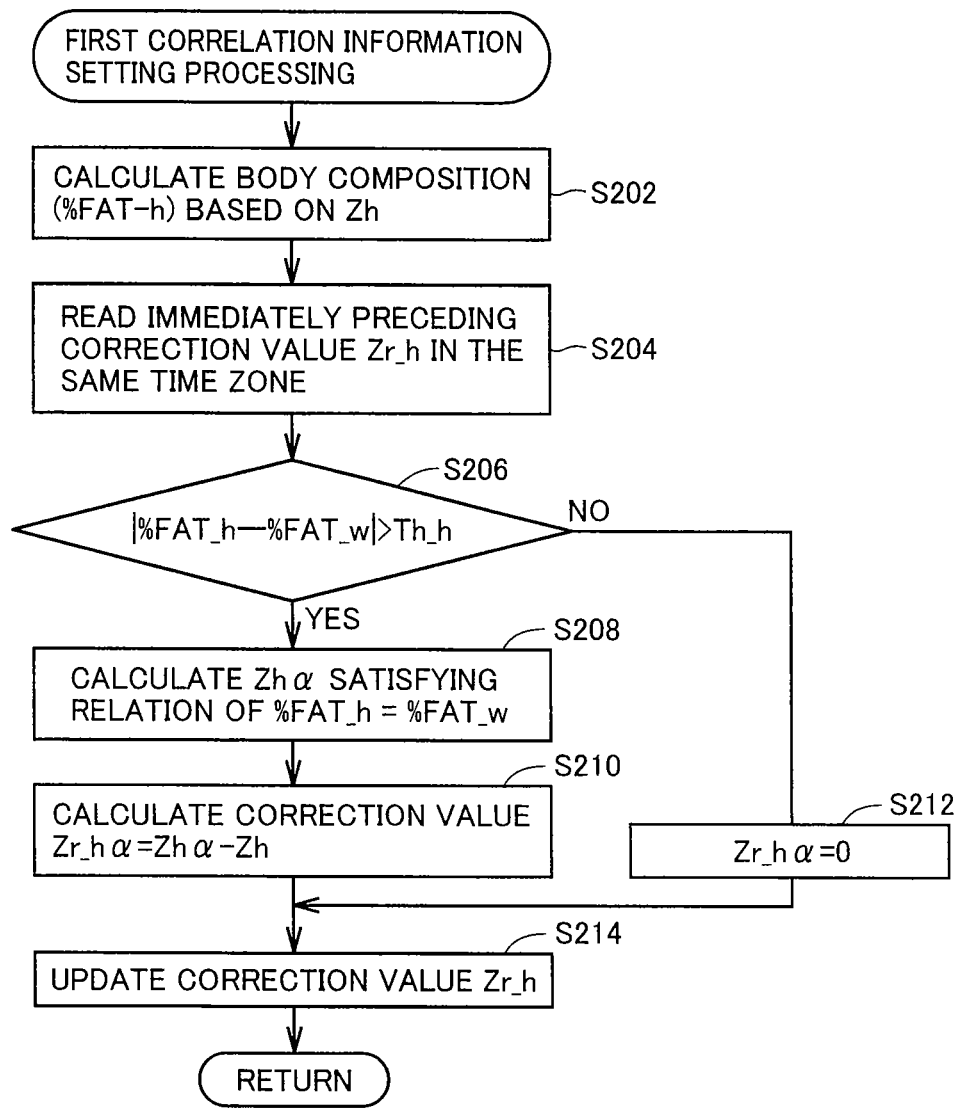
FIG. 9 is a flowchart showing first setting processing in the first embodiment of the present invention.

Referring to FIG. 9 for the first correlation information setting processing in the first embodiment of the present invention, third body composition calculation portion 1061 calculates the whole-body composition, that is, the body fat rate (denoted as "% FAT_h"), based on both-hand impedance Zh (step S202). More specifically, initially, whole-body fat free mass (FFM_h) is calculated by using both-hand impedance Zh, the body information of the subject, and estimation equation (3). Thereafter, the body fat rate (% FAT_h) is calculated. It is also assumed here that the body fat rate is calculated after the fat free mass is calculated, however, the calculation method is not limited as such.

Thereafter, correlation setting portion 106 reads data of correction value Zr_h, which is the immediately preceding correlation information in the same time zone, from memory 14 (step S204).

In succession, correlation setting portion 106 determines whether a differential value between body fat rate % FAT_h calculated in step S202 and body fat rate % FAT_w calculated in step S108 exceeds a predetermined threshold value Th_h (step S206). If it is determined that the differential value exceeds threshold value Th_h (YES in step S206), the process proceeds to step S208. On the other hand, if it is determined that the differential value does not exceed threshold value Th_h (NO in step S206), the process proceeds to step S212. Preferably, threshold value Th_h is set, for example, to about 0.5%, as the difference due to circadian rhythm is about 1%.

In step S208, correction value calculation portion 1062 calculates such impedance Zhα that body fat rate % FAT_h is equal to body fat rate % FAT_w. Thus, the difference between impedance Zα calculated in step S208 and both-hand impedance Zh measured in step S110 is calculated as present correction value Zr_hα (step S210). When the processing in S210 ends, the process proceeds to step S214.

In step S212, present correction value Zr_hα is set to "0".

In step S214, correction value Zr_h is updated. Specifically, for example, new correction value Zr_h is calculated by averaging immediately preceding correction value Zr_h read in step S204 and present correction value Zr_hα (for example, (Zr_h+Zr_hα)/2).

If the correlation information in the same time zone is not stored in memory 14, present correction value Zr_hα is used as correction value Zr_h.

The first correlation information setting processing thus ends.

Figure 10:
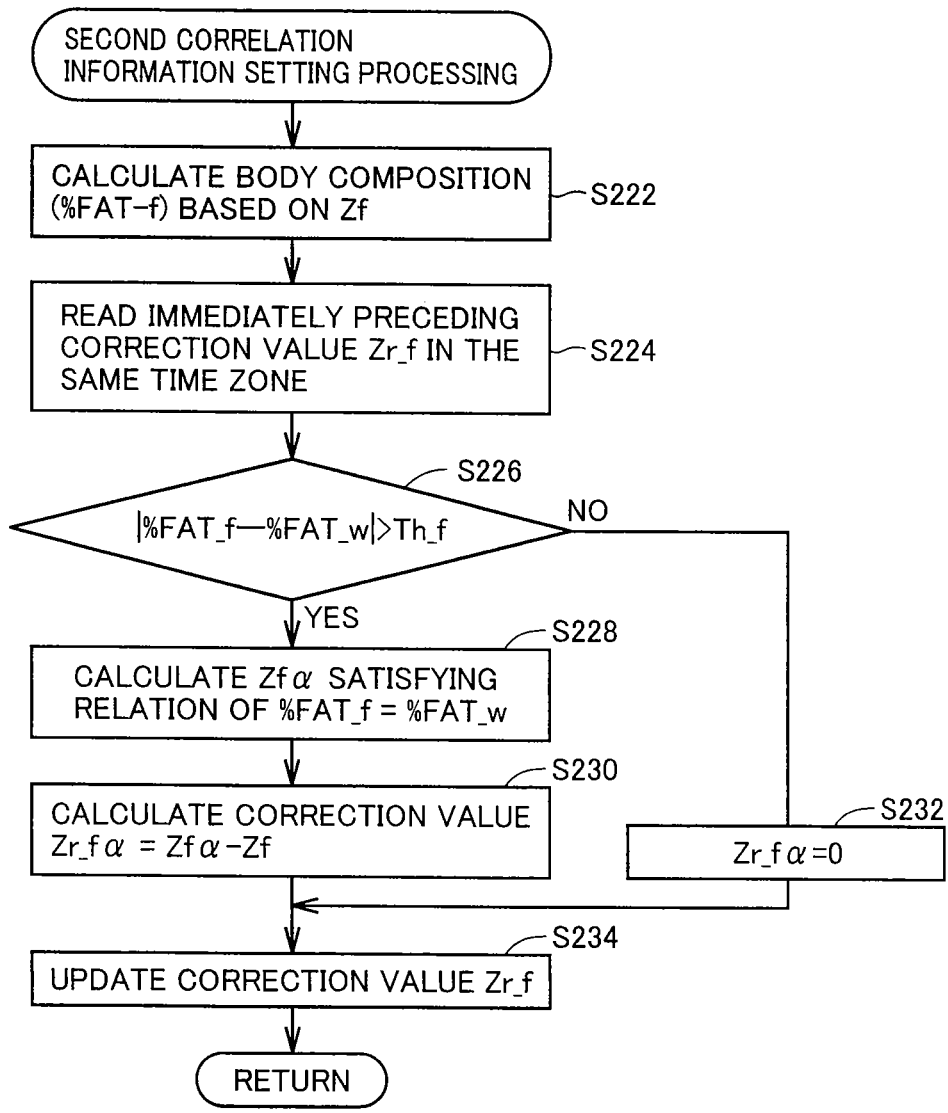
FIG. 10 is a flowchart showing second setting processing in the first embodiment of the present invention.

Referring to FIG. 10 for the second correlation information setting processing in the first embodiment of the present invention, third body composition calculation portion 1061 calculates the whole-body composition, that is, the body fat rate (denoted as "% FAT_f"), based on both-feet impedance Zf (step S222). More specifically, initially, whole-body fat free mass (FFM_f) is calculated by using both-feet impedance Zf, the body information of the subject, and estimation equation (4). Thereafter, the body fat rate (% FAT_f) is calculated by using equation (1). It is also assumed here that the body fat rate is calculated after the fat free mass is calculated, however, the calculation method is not limited as such.

Thereafter, correlation setting portion 106 reads data of correction value Zr_f, which is the immediately preceding correlation information in the same time zone, from memory 14 (step S224).

In succession, correlation setting portion 106 determines whether a differential value between body fat rate % FAT_f calculated in step S222 and body fat rate % FAT_w calculated in step S108 exceeds a predetermined threshold value Th_f (step S226). If it is determined that the differential value exceeds threshold value Th_f (YES in step S226), the process proceeds to step S228. On the other hand, if it is determined that the differential value does not exceed threshold value Th_f (NO in step S226), the process proceeds to step S232. Preferably, threshold value Th_f is also set, for example, to about 0.5%, as the difference due to circadian rhythm is about 1%.

In step S228, correction value calculation portion 1062 calculates such impedance Zfα that body fat rate % FAT_f is equal to body fat rate % FAT_w. Thus, the difference between impedance Zfα calculated in step S228 and both-feet impedance Zf measured in step S112 is calculated as present correction value Zr_fα (step S230). When the processing in S230 ends, the process proceeds to step S234.

In step S232, present correction value Zr_fα is set to "0".

In step S234, correction value Zr_f is updated. Specifically, for example, new correction value Zr_f is calculated by averaging immediately preceding correction value Zr_f read in step S224 and present correction value Zr_fα (for example, (Zr_f+Zr_fα)/2).

If the correlation information in the same time zone is not stored in memory 14, present correction value Zr_fα is used as correction value Zr_f.

The second correlation information setting processing thus ends.

In the present embodiment, the correction value is updated by averaging the immediately preceding correction value and the present correction value, however, updating is not limited to such a method. For example, all the past correction values may be read and averaged. Alternatively, correction values within a prescribed period may be read and averaged. Alternatively, the present correction value may simply be found without averaging.

In addition, body fat rate % FAT_w used in steps S206 and S208 in the first correlation information setting processing and steps S226 and S228 in the second correlation information setting processing may be an average value within a prescribed period, of measurement values in the whole-body measurement mode.

Figure 11:
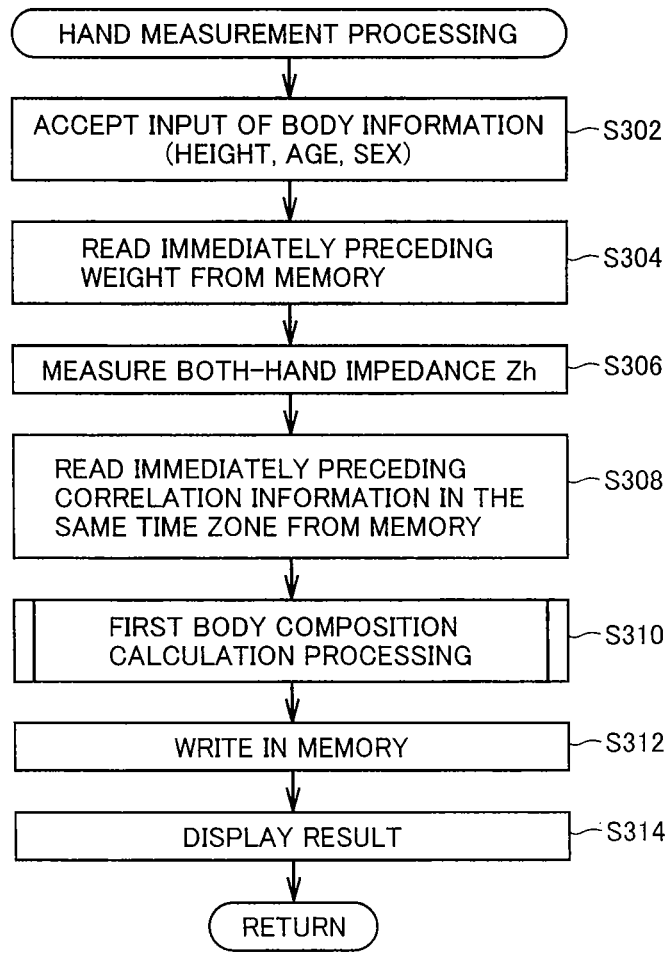
FIG. 11 is a flowchart showing hand measurement processing in the first to third embodiments of the present invention.

Referring to FIG. 11 for the hand measurement processing in the first embodiment of the present invention, control portion 12 accepts input of the body information (height, age, sex) of the subject (step S302). Thereafter, control portion 12 reads the immediately preceding weight from memory 14 (step S304). Thus, time and effort for input of a weight value by the subject can be saved. Data of the weight read here may be immediately preceding data in the same time zone or may simply be immediately preceding data (regardless of the time zone).

Thereafter, two-limb impedance measurement portion 102 measures both-hand impedance Zh (step S306). In succession, control portion 12 reads correction value Zr_h, which is the immediately preceding (most recent) correlation information in the same time zone, from memory 14 (step S308). In succession, the first body composition calculation processing is performed (step S310). Here, specific processing in the first body composition calculation processing in step S310 will be described with reference to FIG. 12.

Figure 12:
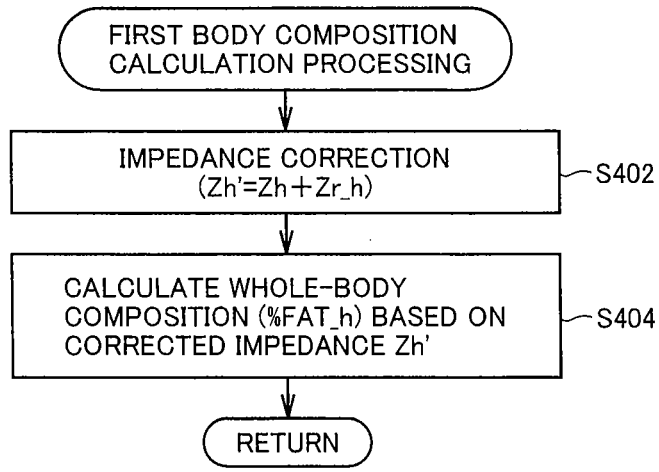
FIG. 12 is a flowchart showing first body composition calculation processing in the first embodiment of the present invention.

Referring to FIG. 12, correction portion 104 corrects both-hand impedance Zh measured in step S306 (step S402). Specifically, corrected impedance Zh' is calculated by adding correction value Zr_h read as the correlation information in step S308 to both-hand impedance Zh.

Thereafter, second body composition calculation portion 105 calculates whole-body composition, that is, body fat rate (% FAT_h), based on corrected impedance Zh' (step S404). More specifically, the body fat rate is calculated based on impedance Zh', the body information of the subject, and equations (1) and (3) above.

Referring again to FIG. 11, when the first body composition calculation processing ends, control portion 12 writes the measurement result or the like in memory 14, in association with the time zone determined in step S4 (step S312). Finally, control portion 12 displays the measurement result (the body fat rate) on display portion 15 (step S314).

The hand measurement processing thus ends.

Figure 13:
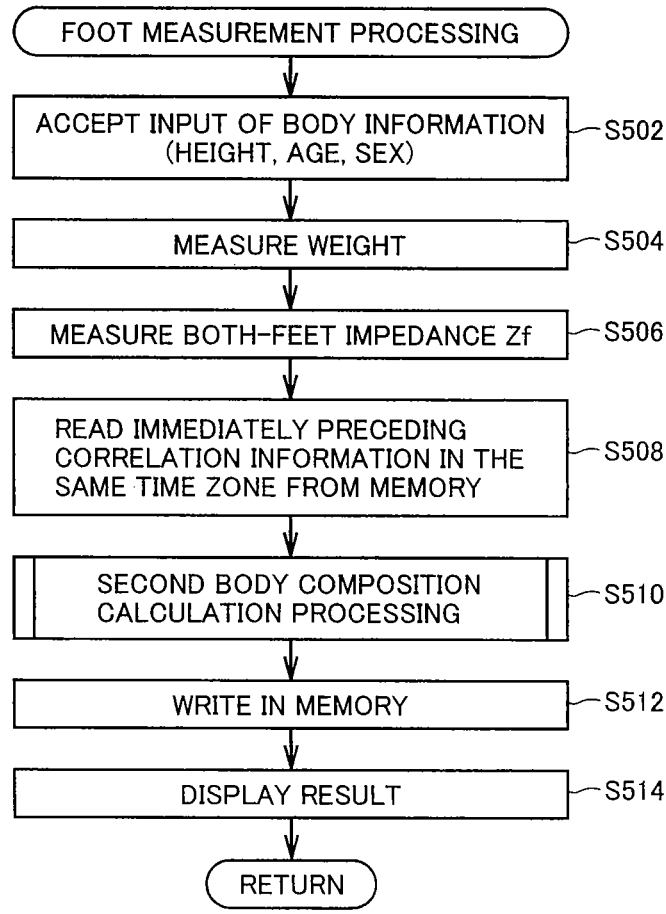
FIG. 13 is a flowchart showing foot measurement processing in the first to third embodiments of the present invention.

Referring to FIG. 13 for foot measurement processing in the first embodiment of the present invention, control portion 12 accepts input of the body information (height, age, sex) from the subject (step S502). Thereafter, control portion 12 measures the weight with weight measurement portion 22 (step S504).

Thereafter, two-limb impedance measurement portion 102 measures both-feet impedance Zf (step S506). In succession, control portion 12 reads correction value Zr_f, which is the immediately preceding correlation information in the same time zone, from memory 14 (step S508). In succession, the second body composition calculation processing is performed (step S510). Here, specific processing in the second body composition calculation processing in step S510 will be described with reference to FIG. 14.

Figure 14:
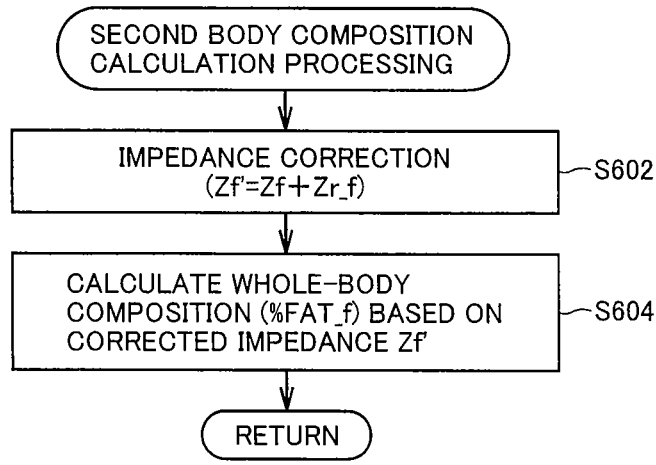
FIG. 14 is a flowchart showing second body composition calculation processing in the first embodiment of the present invention.

Referring to FIG. 14, correction portion 104 corrects both-feet impedance Zf measured in step S506 (step S602). Specifically, corrected impedance Zf' is calculated by adding correction value Zr_f read as the correlation information in step S508 to both-feet impedance Zf.

Thereafter, second body composition calculation portion 105 calculates whole-body composition, that is, body fat rate (% FAT_f), based on corrected impedance Zf' (step S604). More specifically, the body fat rate is calculated based on impedance Zf', the body information of the subject, and equations (1) and (4) above.

Referring again to FIG. 13, when the second body composition calculation processing ends, control portion 12 writes the measurement result or the like in memory 14, in association with the time zone (step S512). Finally, control portion 12 displays the measurement result (the body fat rate) on display portion 15 (step S514).

The foot measurement processing thus ends.

As described above, in the first embodiment of the present invention, in the whole-body measurement mode, the correction value for the two-limb impedance is set as the correlation information. Namely, such a correction value for the two-limb impedance that the whole-body composition based on the whole-body impedance and estimation equation (2) above, that has been calculated in the whole-body measurement mode, is equal to the whole-body composition based on the two-limb impedance and estimation equations (3) and (4) above is set as the correlation information. Then, in the simplified measurement mode as well, highly reliable whole-body composition corresponding to the user (subject) can be calculated.

In addition, in the present embodiment, as the correlation information is set for each time zone of measurement, influence of circadian rhythm can be accommodated. Namely, as such a correction value for the two-limb impedance that the whole-body composition based on the whole-body impedance and estimation equation (2) is equal to the whole-body composition based on the two-limb impedance and estimation equation (3), (4) is set as the correlation information, a highly accurate numeric value of the body composition, comparable to the whole-body composition calculated based on the whole-body impedance and estimation equation (2), can be estimated also in the simplified measurement mode. Thus, even if the subject measures the whole-body composition in the simplified measurement mode, the subject can also check variation in the whole-body composition without concern for influence of circadian rhythm.

Moreover, in the present embodiment, if the correlation information in the same time zone set within a prescribed period (such as seven days) is not stored in memory 14 (NO in step S8), notification to urge the subject to set the whole-body measurement mode is given. The notification method, however, is not limited as such. For example, notification that use in the simplified measurement mode is prohibited may be given. Alternatively, the whole-body composition is calculated without performing correction processing and notification to that effect (correction processing is not applicable) may be given. More specifically, for example, if a mode where the whole-body composition is measured simply by using two-limb impedance is referred to as "simple two-limb measurement mode," notification to the effect that the measurement result in the simple two-limb measurement mode is provided may be given.

Alternatively, in the present embodiment, in order to improve reliability, whether or not there is correlation information in the same time zone set within a prescribed period is determined, however, whether or not there is correlation information in the same time zone may simply be determined.

In the present embodiment, the body information is input for each measurement, however, the body information once input may be stored in memory 14 and input thereafter may not be made.

In addition, in the present embodiment, the correlation information is set for each time zone, however, the correlation information may be set regardless of the time zone. Alternatively, the correlation information may be set for each measurement condition other than the time zone (such as before exercise and after exercise).

Moreover, in the present embodiment, in setting the correlation information, the correction value for the two-limb impedance is calculated based on body fat rate % FAT_w and body fat rate % FAT_h, f, however, it may be calculated based on fat free mass FFM_w and fat free mass FFM_h, f. Alternatively, a correction value for composition (such as fat free mass) of two limbs may be calculated as the correlation information. Alternatively, a correction value for a potential difference between the two limbs may be calculated as the correlation information.

Further, in the present embodiment, the correlation information is stored in association with the time zone and the correlation information corresponding to the time zone determined in the simplified measurement mode is read. Alternatively, however, the correlation information may be stored in association with the time and the correlation information corresponding to the time zone determined in the simplified measurement mode may be read.

In addition, in the present embodiment, the simplified measurement mode includes both of the hand-simplified measurement mode and the foot-simplified measurement mode, however, any one of these may be provided. For example, if solely the hand-simplified measurement mode is provided, in the mode selection processing described above, the "whole-body measurement mode" may simply be selected if connector 18 and connector 31 are connected to each other, and otherwise the "hand-simplified measurement mode" may simply be selected. Similarly, if solely the foot-simplified measurement mode is provided, the "foot-simplified measurement mode" may be selected if upper-limb unit 1 is housed in housing portion 20, and otherwise the "whole-body measurement mode" may be selected. Alternatively, a mode for measuring body composition based on impedance between right hand and left foot and the like may further be provided.

Second Embodiment

A second embodiment of the present invention will now be described.

In the first embodiment above, the correction value for the two-limb impedance is employed as the correlation information. In the second embodiment, correlation between the whole-body composition calculated based on the whole-body impedance and the whole-body composition calculated based on the two-limb impedance is employed as the correlation information. Appearance and hardware configuration of the body composition monitor in the second embodiment are the same as those of body composition monitor 100 in the first embodiment. Therefore, description here will be given also by using the reference characters shown in FIGS. 1 and 2.

Differences from the first embodiment will be described hereinafter.

Here, a control portion in the second embodiment is different from control portion 12 in the first embodiment in functions. Therefore, in the present embodiment, the control portion is denoted as a control portion 12A.

Figure 15:
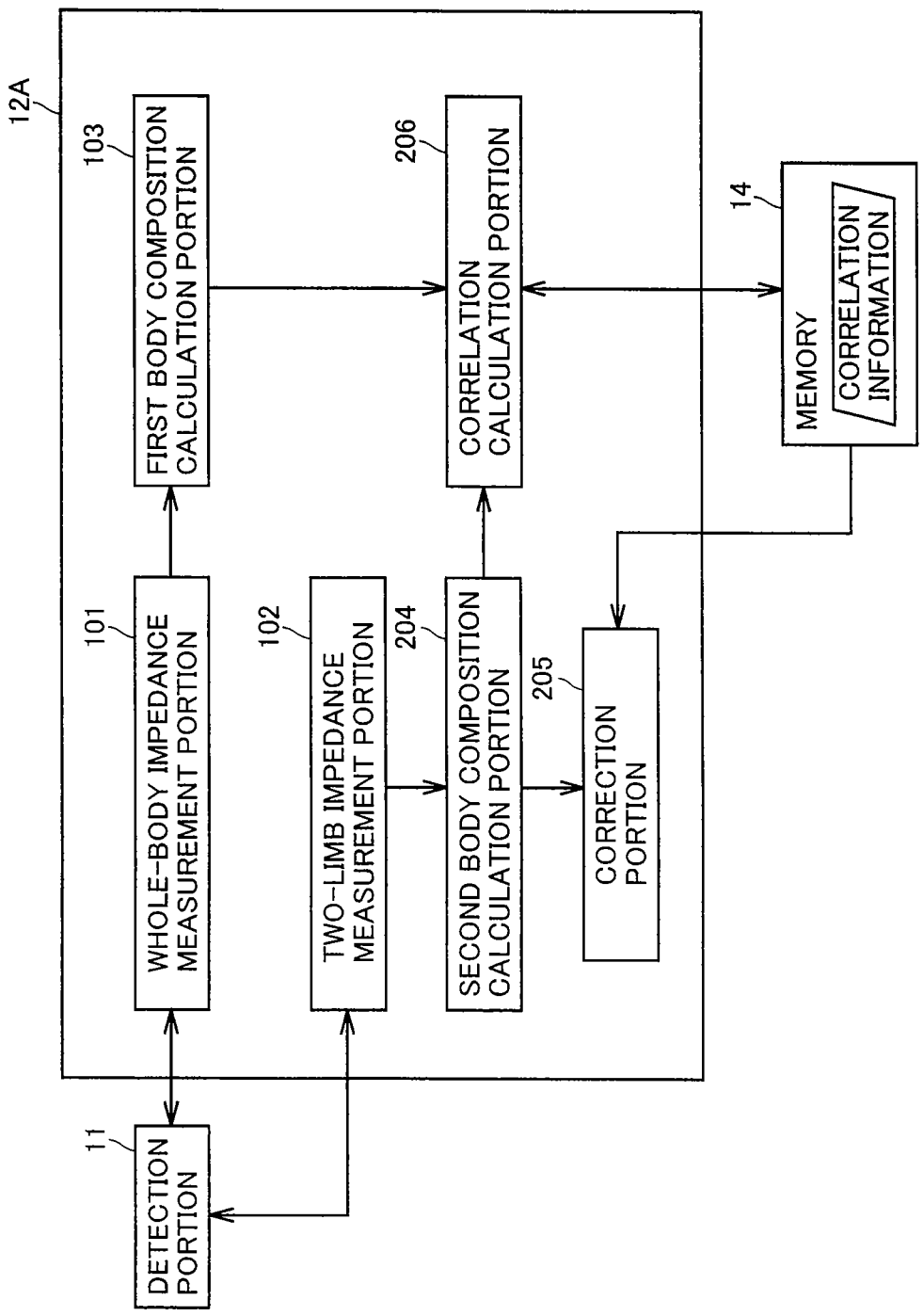
FIG. 15 is a functional block diagram of the body composition monitor in the second embodiment of the present invention.

Referring to FIG. 15, control portion 12A of body composition monitor 100 in the second embodiment of the present invention includes whole-body impedance measurement portion 101, two-limb impedance measurement portion 102 and first body composition calculation portion 103 as in the first embodiment. In addition, control portion 12A includes a second body composition calculation portion 204, a correction portion 205, and a correlation calculation portion 206 instead of correction portion 104, second body composition calculation portion 105, and correlation setting portion 106 in the first embodiment.

Second body composition calculation portion 204 calculates the whole-body composition based on the two-limb impedance measured by two-limb impedance measurement portion 102.

In the simplified measurement mode, correction portion 205 corrects the whole-body composition calculated by second body composition calculation portion 204 based on the correlation information stored in memory 14 (correlation between the whole-body composition calculated based on the whole-body impedance and the whole-body composition calculated based on the two-limb impedance).

In the whole-body measurement mode, correlation calculation portion 206 calculates correlation between the whole-body composition calculated by second body composition calculation portion 204 and the whole-body composition calculated by first body composition calculation portion 103. Specifically, correlation calculation portion 206 calculates, for example, correlation between fat free mass FFM_w and fat free mass FFM_h, f. A detailed calculation method will be described later.

Figure 16:
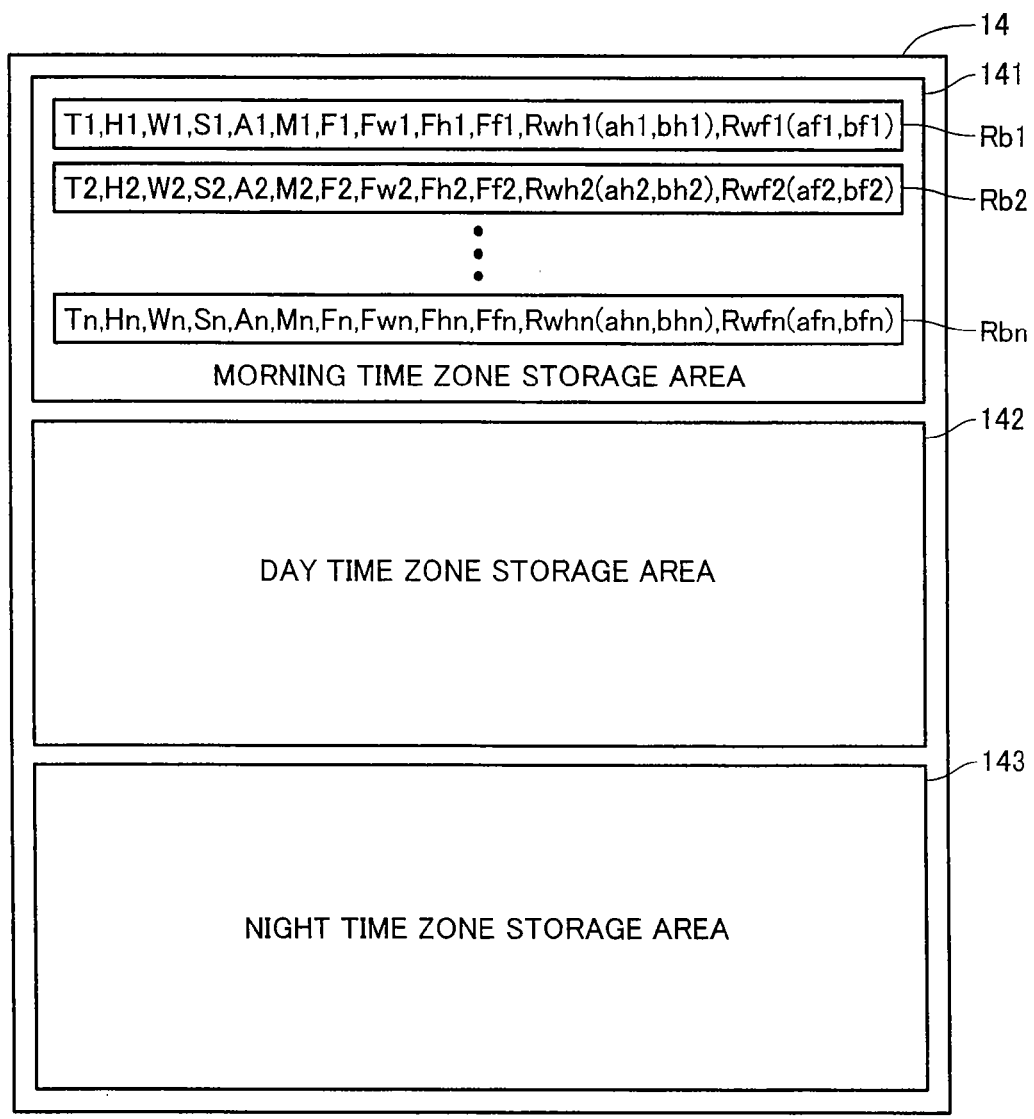
FIG. 16 illustrates an exemplary data structure in a memory of the body composition monitor in the second embodiment of the present invention.

Referring to FIG. 16, as in the first embodiment, memory 14 in body composition monitor 100 in the second embodiment of the present invention includes morning time zone storage area 141 for storing a measurement result in the morning time zone, day time zone storage area 142 for storing a measurement result in the day time zone, and night time zone storage area 143 for storing a measurement result in the night time zone.

When the body composition measurement processing is performed, a record Rb (Rb1, Rb2, . . . , Rbn) including time and day data T of measurement, height input value data H serving as the body information, weight value data W serving as the body information, sex data S serving as the body information, age data A serving as the body information, measurement mode data M, whole-body composition data F serving as the measurement result, whole-body fat free mass data Fw, Fh, Ff, correlation information Rwh, and correlation information Rwf is stored in an area in accordance with the time zone of measurement.

As in the first embodiment, whole-body composition data F represents the final measurement result of the body composition, and represents data of the body fat rate calculated by first body composition calculation portion 103 or data of the body fat rate corrected by correction portion 205. Namely, if measurement mode data M indicates "0" (whole-body measurement mode), it indicates data of results of calculation by first body composition calculation portion 103. If measurement mode data M indicates "1" or "2" (simplified measurement mode), it indicates data of results of calculation by correction portion 205.

Whole-body fat free mass data Fw is data of fat free mass FFM_w calculated based on whole-body impedance Zw and estimation equation (2) by first body composition calculation portion 103, when measurement mode data M indicates "0" (whole-body measurement mode). Fat free mass FFM_w is calculated when the body fat rate is calculated in step S108. Whole-body fat free mass data Fh is data of fat free mass FFM_h calculated based on both-hand impedance Zh and estimation equation (3) by second body composition calculation portion 204, when measurement mode data M indicates "0" (whole-body measurement mode). Whole-body fat free mass data Ff is data of fat free mass FFM_f calculated based on both-feet impedance Zf and estimation equation (4) by second body composition calculation portion 204, when measurement mode data M indicates "0" (whole-body measurement mode).

In the second embodiment, data indicating correlation coefficients ah, bh and data indicating correlation coefficients af, bf, which will be described later, are stored in correlation information Rwh and correlation information Rwf, respectively.

Figure 17:
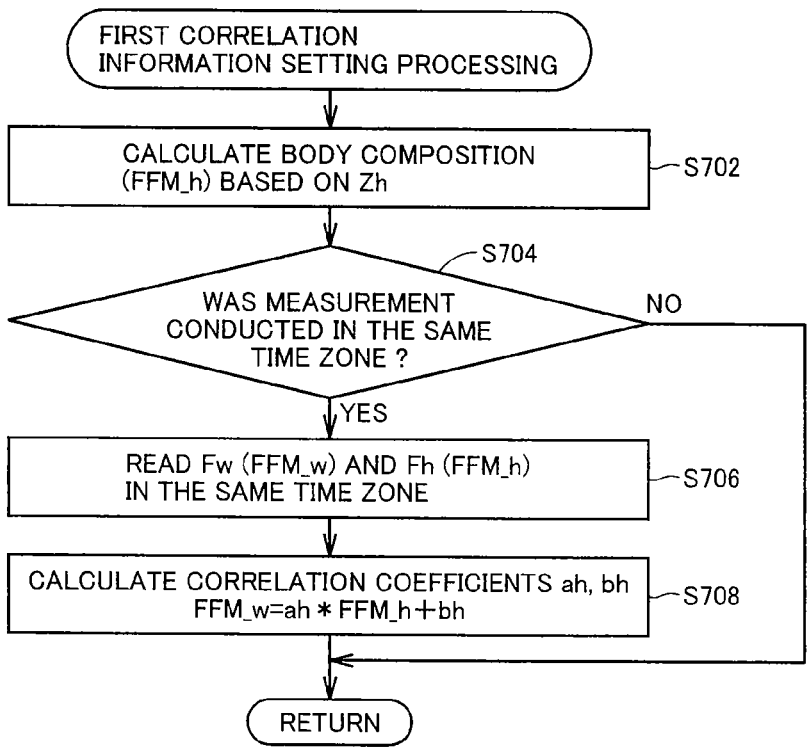
FIG. 17 is a flowchart showing first setting processing in the second embodiment of the present invention.

Referring to FIG. 17 for first correlation information setting processing in the second embodiment of the present invention, second body composition calculation portion 204 calculates the whole-body fat free mass (FFM_h) based on both-hand impedance Zh (step S702). Thereafter, control portion 12A determines whether measurement in the whole-body measurement mode was conducted in the same time zone or not (S704). More specifically, whether or not record Rb in which mode data M indicates "0" is present among records Rb stored in the same time zone is determined. If it is determined that measurement was conducted (YES in S704), the process proceeds to S706. On the other hand, if it is determined that measurement was not conducted (NO in S704), the process ends.

In step S706, correlation calculation portion 206 reads from memory 14, all whole-body fat free mass (FFM_w) data Fw and whole-body fat free mass (FFM_h) data Fh in the same time zone.

In succession, correlation calculation portion 206 calculates correlation between whole-body fat free mass FFM_w and whole-body fat free mass FFM_h (step S708). More specifically, such correlation coefficients ah, bh as satisfying the correlation equation below are calculated based on the fat free masses calculated in steps S108 and S702 and the fat free masses read in step S706.

$$FFM\_w = ah * FFM\_h + bh$$

The first correlation information setting processing thus ends.

It is noted that the correlation coefficient can be calculated based on each piece of data, for example, by using a least squares method.

Figure 18:
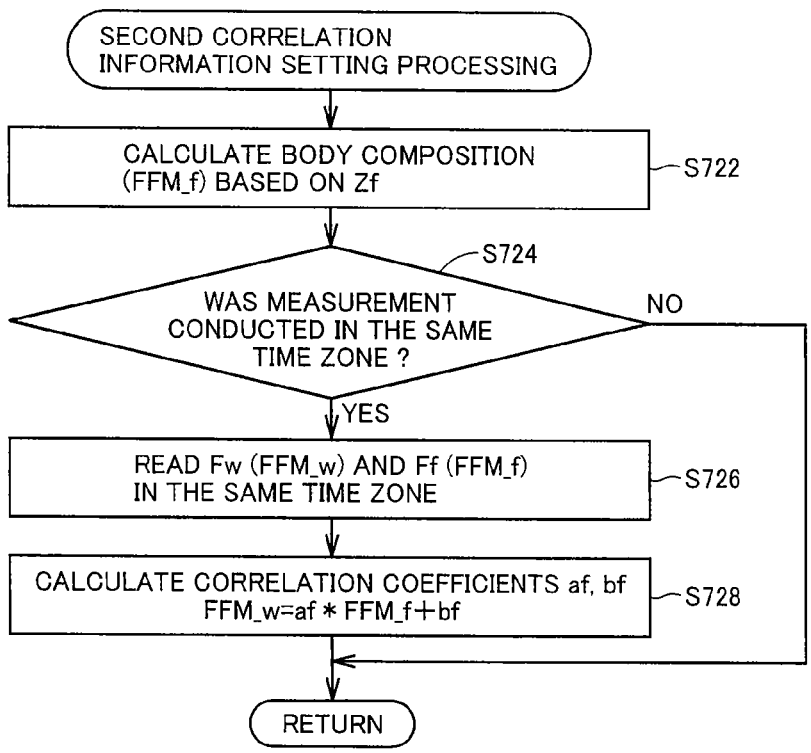
FIG. 18 is a flowchart showing second setting processing in the second embodiment of the present invention.

Referring to FIG. 18 for second correlation information setting processing in the second embodiment of the present invention, second body composition calculation portion 204 calculates the whole-body fat free mass (FFM_f) based on both-feet impedance Zf (step S722). Thereafter, control portion 12A determines whether measurement in the whole-body measurement mode was conducted in the same time zone or not (S724). If it is determined that measurement was conducted (YES in S724), the process proceeds to S726. On the other hand, if it is determined that measurement was not conducted (NO in S724), the process ends.

In step S726, correlation calculation portion 206 reads all whole-body fat free mass (FFM_w) data Fw and whole-body fat free mass (FFM_f) data Ff in the same time zone.

In succession, correlation calculation portion 206 calculates correlation between the whole-body fat free mass (FFM_w) and the whole-body fat free mass (FFM_f) (step S728). More specifically, such correlation coefficients af, bf as satisfying the correlation equation below are calculated based on the fat free masses calculated in steps S108 and S722 and the fat free masses read in step S726.

$$FFM\_f = af * FFM\_f + bf$$

It is noted that the processing in steps S722 to S728 correspond to the processing in steps S702 to S708 shown in FIG. 17, respectively.

As the first and second correlation information setting processing as above is performed in the second embodiment, correlation coefficients ah, bh are stored as correlation information Rwh and correlation coefficients af, bf are stored as correlation information Rwf in step S118 in FIG. 8. Moreover, body fat rate % FAT_w % calculated in step S108 is stored as body fat rate data F. Further, fat free masses FFM_w, FFM_h, and FFM_f calculated in steps S108, S702, and S722 are stored as fat free mass data Fw, Fh, and Ff respectively.

Figure 19:
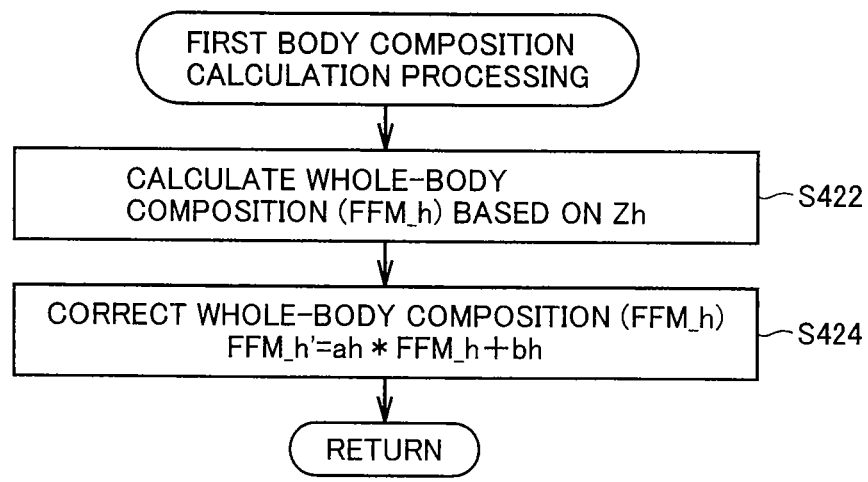
FIG. 19 is a flowchart showing first body composition calculation processing in the second embodiment of the present invention.

In the first body composition calculation processing in the second embodiment of the present invention shown in FIG. 19, it is assumed that immediately preceding correlation coefficients ah, bh in the same time zone have been read in step S308.

Referring to FIG. 19, second body composition calculation portion 204 calculates whole-body fat free mass FFM_h based on both-hand impedance Zh measured in step S306 (step S422). More specifically, the fat free mass is calculated based on both-hand impedance Zh, the body information of the subject, and equation (3) above.

Thereafter, correction portion 205 corrects whole-body fat free mass FFM_h calculated in step S422 based on correlation coefficients ah, bh read as the correlation information in step S308 (step S424). More specifically, corrected whole-body fat free mass FFM_h' is calculated with the following equation.

$$FFM\_h'=ah*FFM\_h+bh$$

In step S424, body fat rate % FAT_h is further calculated by substituting corrected fat free mass FFM_h' into equation (1) above.

As the processing above is performed, body fat rate % FAT_h calculated in step S424 is stored in memory 14 as whole-body composition data F in step S312, and presented to the subject in step S314.

Figure 20:
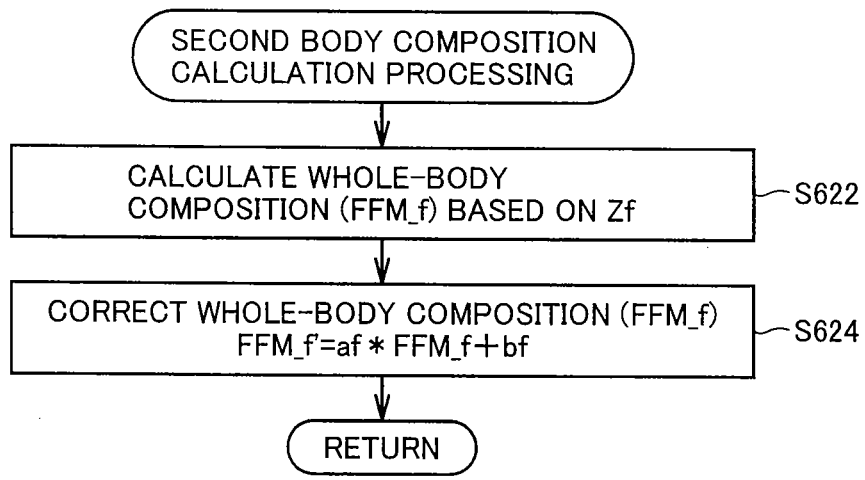
FIG. 20 is a flowchart showing second body composition calculation processing in the second embodiment of the present invention.

In the second body composition calculation processing in the second embodiment of the present invention shown in FIG. 20, it is assumed that immediately preceding correlation coefficients af, bf in the same time zone have been read in step S508.

Referring to FIG. 20, second body composition calculation portion 204 calculates whole-body fat free mass FFM_f based on both-feet impedance Zf measured in step S506 (step S622). More specifically, the fat free mass is calculated based on both-feet impedance Zf, the body information of the subject, and equation (4) above.

Thereafter, correction portion 205 corrects whole-body fat free mass FFM_f calculated in step S622 based on correlation coefficients af, bf read as the correlation information in step S508 (step S624). More specifically, corrected whole-body fat free mass FFM_f' is calculated with the following equation.

$$FFM\_f'=af*FFM\_f+bf$$

In step S624, body fat rate % FAT_f is further calculated by substituting corrected fat free mass FFM_f' into equation (1) above.

As the processing above is performed, body fat rate % FAT_f calculated in step S624 is stored in memory 14 as whole-body composition data F in step S512, and presented to the subject in step S514.

As described above, in the second embodiment of the present invention, in the whole-body measurement mode, correlation between the whole-body composition based on the whole-body impedance and the whole-body composition based on the two-limb impedance is set as the correlation information. Then, in the simplified measurement mode as well, highly reliable whole-body composition corresponding to the subject can be calculated.

In the present embodiment, description is given assuming that correlation between fat free mass FFM_w and fat free mass FFM_h or FFM_f is calculated, however, correlation between body fat rate % FAT_w and body fat rate % FAT_h or % FAT_f may be calculated.

In addition, in the present embodiment, fat free mass data Fw and fat free mass data Fh, Ff stored in the storage area for the same time zone are all read in steps S706 and S726, however, for example, data within a prescribed period in the past may be read. Alternatively, record Rb may further include all fat free mass data Fw, Fh, and Ff within a prescribed period. Then, immediately preceding data in the same time zone should only be read.

Third Embodiment

A third embodiment of the present invention will now be described.

In the first embodiment, the correction value for the two-limb impedance is employed as the correlation information. In addition, in the second embodiment, correlation between the whole-body composition calculated based on the whole-body impedance and the whole-body composition calculated based on the two-limb impedance is employed as the correlation information.

In the third embodiment, correlation between the whole-body impedance and the two-limb impedance is employed as the correlation information. Appearance and hardware configuration of the body composition monitor in the third embodiment are the same as those of body composition monitor 100 in the first and second embodiments. Therefore, description here will be given also by using the reference characters shown in FIGS. 1 and 2.

Differences from the first embodiment will mainly be described in the following.

Here, a control portion in the third embodiment is different from control portion 12 in the first embodiment and control portion 12A in the second embodiment in functions. Therefore, in the present embodiment, the control portion is denoted as a control portion 12B.

Figure 21:
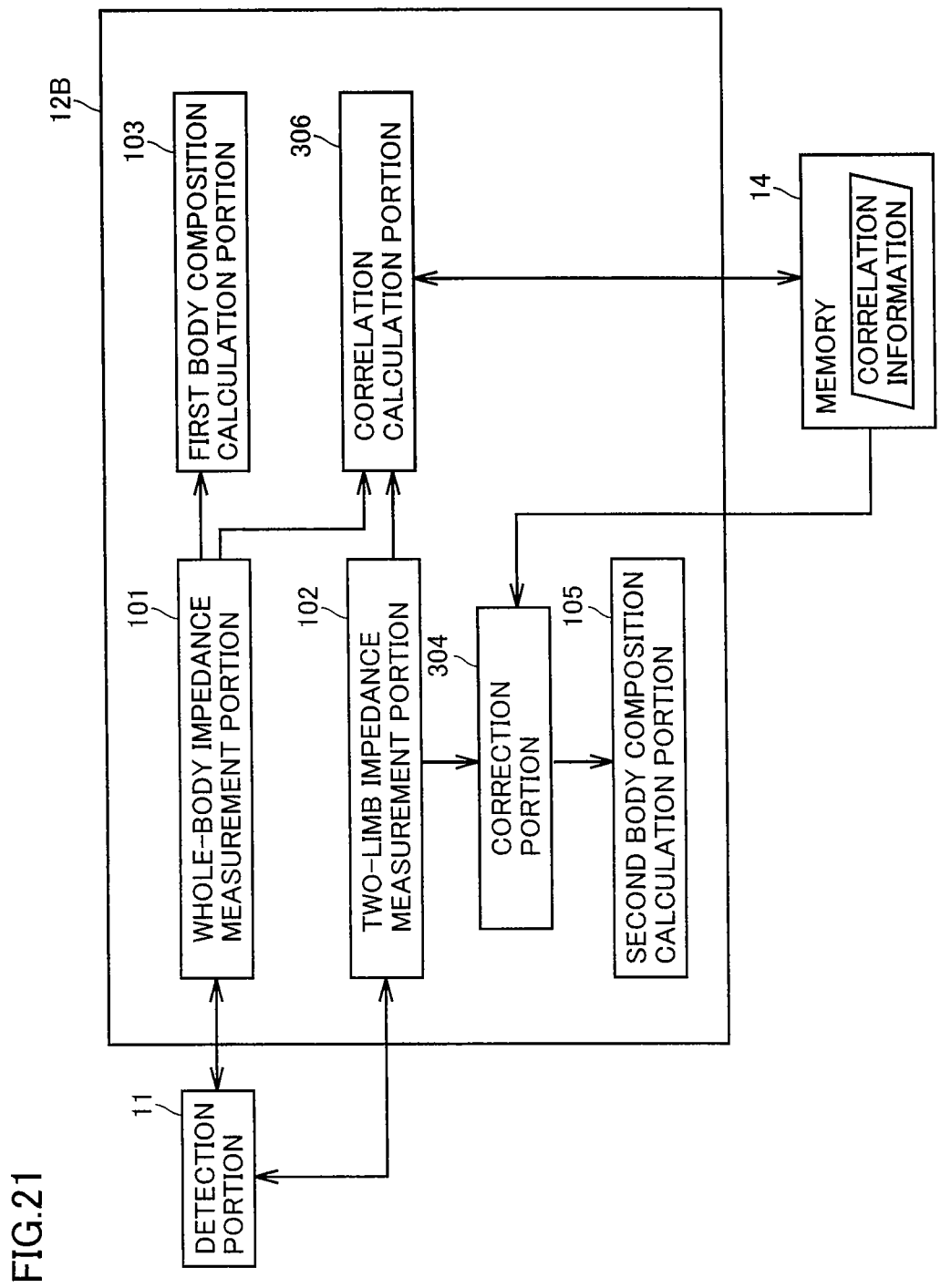
FIG. 21 is a functional block diagram of the body composition monitor in the third embodiment of the present invention.

Referring to FIG. 21, control portion 12B includes whole-body impedance measurement portion 101, two-limb impedance measurement portion 102, first body composition calculation portion 103, and second body composition calculation portion 105 as in the first embodiment. In addition, control portion 12B includes a correction portion 304 and a correlation calculation portion 306 instead of correction portion 104 and correlation setting portion 106 in the first embodiment.

In the simplified measurement mode, correction portion 304 corrects the two-limb impedance measured by two-limb impedance measurement portion 102 based on the correlation information stored in memory 14 (correlation between the whole-body impedance and the two-limb impedance).

Correlation calculation portion 306 calculates correlation between the whole-body impedance measured by whole-body impedance measurement portion 101 and the two-limb impedance measured by two-limb impedance measurement portion 102 in the whole-body measurement mode.

Figure 22:
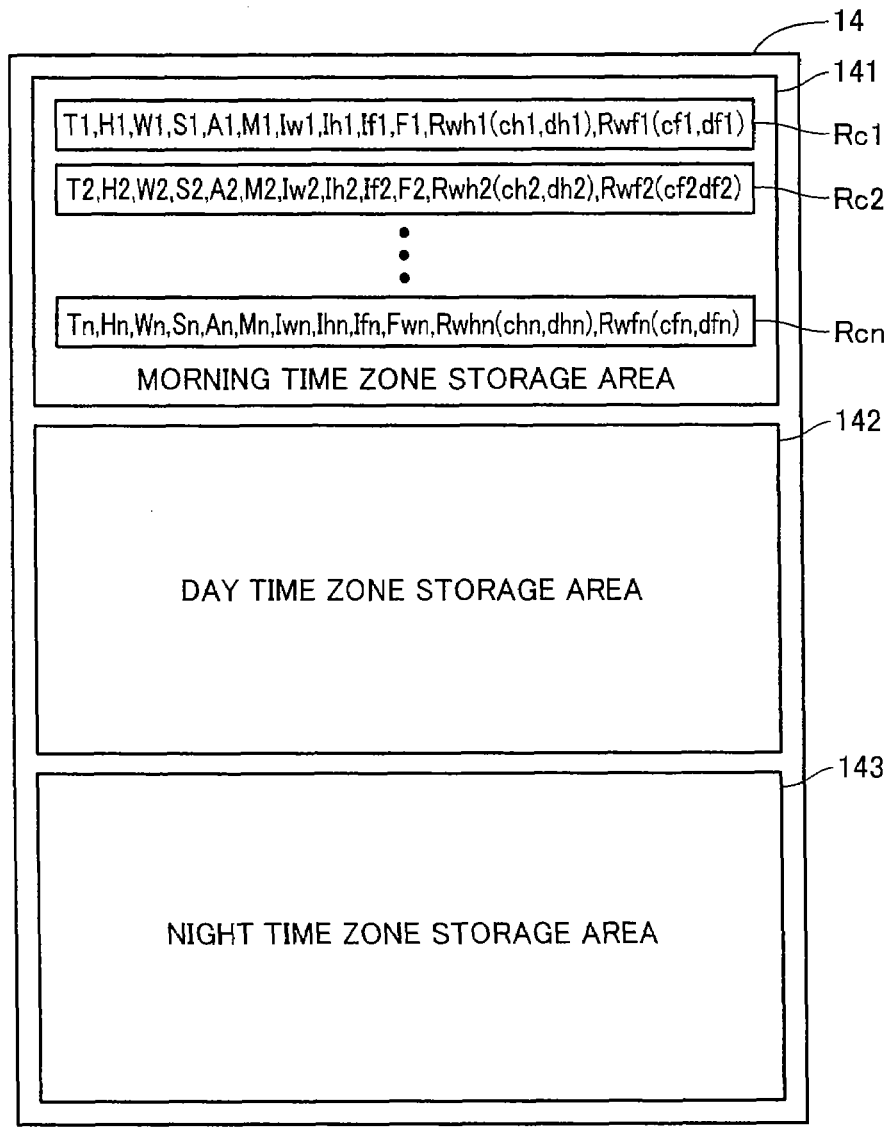
FIG. 22 illustrates an exemplary data structure in a memory of the body composition monitor in the third embodiment of the present invention.

Referring to FIG. 22, as in the first embodiment, memory 14 in body composition monitor 100 in the third embodiment of the present invention includes morning time zone storage area 141 for storing a measurement result in the morning time zone, day time zone storage area 142 for storing a measurement result in the day time zone, and night time zone storage area 143 for storing a measurement result in the night time zone.

When the body composition measurement processing is performed, a record Rc (Rc1, Rb2, . . . , Rcn) including time and day data T of measurement, height input value data H serving as the body information, weight value data W serving as the body information, sex data S serving as the body information, age data A serving as the body information, measurement mode data M, data Iw representing whole-body impedance Zw, data Ih representing both-hand impedance Zh, data If representing both-feet impedance Zf, whole-body composition data F serving as the measurement result, correlation information Rwh, and correlation information Rwf is stored in an area in accordance with the time zone of measurement.

As in the first embodiment, whole-body composition data F represents the final measurement result of the body composition, and represents data of the body fat rate calculated by first body composition calculation portion 103 or second body composition calculation portion 105.

Data Iw is data representing whole-body impedance Zw measured by whole-body impedance measurement portion 101, when measurement mode data M indicates "0" (whole-body measurement mode). Data Ih is data representing both-hand impedance Zh measured by two-limb impedance measurement portion 102, when measurement mode data M indicates "0" (whole-body measurement mode). Data If is data representing both-feet impedance Zf measured by two-limb impedance measurement portion 102, when measurement mode data M indicates "0" (whole-body measurement mode).

In the third embodiment, data indicating correlation coefficients ch, dh and data indicating correlation coefficients cf, df, which will be described later, are stored in correlation information Rwh and correlation information Rwf, respectively.

Figure 23:
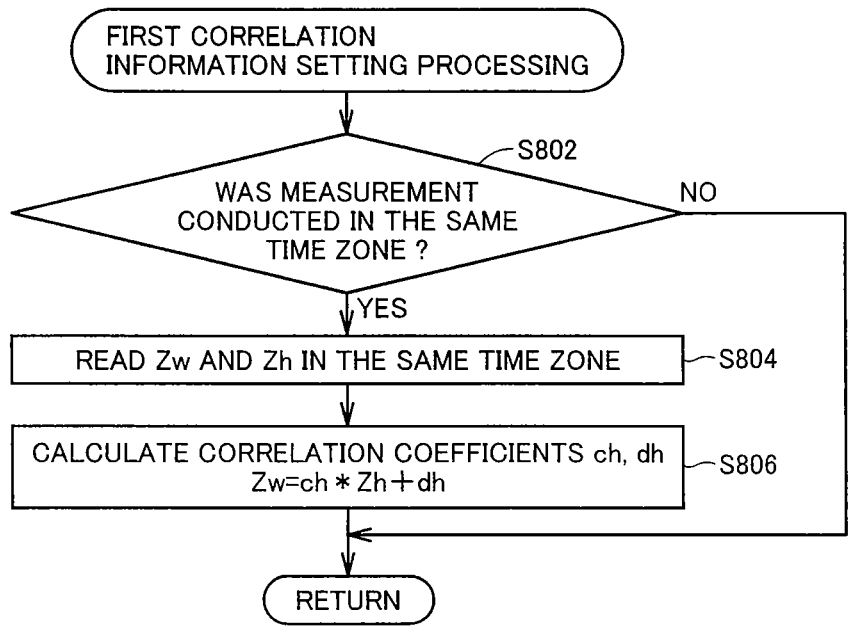
FIG. 23 is a flowchart showing first setting processing in the third embodiment of the present invention.

Referring to FIG. 23 for first correlation information setting processing in the third embodiment of the present invention, initially, control portion 12B determines whether measurement in the whole-body measurement mode was conducted or not in the same time zone (S802). More specifically, whether record Rc in which measurement mode data M indicates the whole-body measurement mode is present among records Rc stored in the storage area for the same time zone is determined. If it is determined that measurement was conducted (YES in S802), the process proceeds to S804. On the other hand, if it is determined that measurement was not conducted (NO in S802), the process ends.

In step S804, correlation calculation portion 306 reads from memory 14, all data Iw of whole-body impedance Zw and data Ih of both-hand impedance Zh in the same time zone.

In succession, correlation calculation portion 306 calculates such correlation coefficients ch, dh as satisfying the following correlation equation, based on whole-body impedance Zw and both-hand impedance Zh measured in steps S106 and S110 respectively and on whole-body impedance Zw and impedance Zh read in step S804 (S806).

$$Zw = ch*Zh + dh$$

The first correlation information setting processing thus ends.

Figure 24:
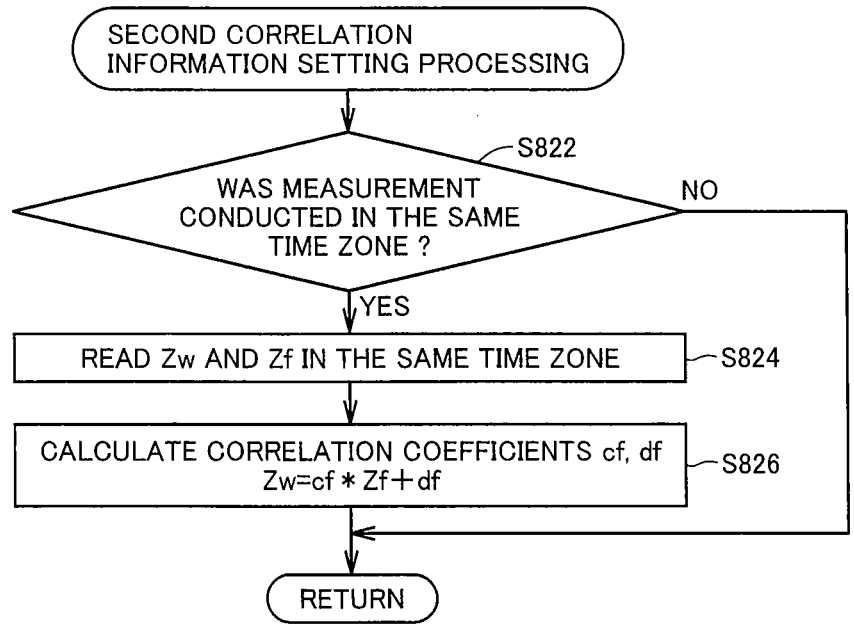
FIG. 24 is a flowchart showing second setting processing in the third embodiment of the present invention.

Referring to FIG. 24 for second correlation information setting processing in the third embodiment of the present invention, initially, control portion 12B determines whether measurement in the whole-body measurement mode was conducted or not in the same time zone (S822). More specifically, whether record Rc in which measurement mode data M indicates the whole-body measurement mode is present among records Rc stored in the storage area for the same time zone is determined. If it is determined that measurement was conducted (YES in S822), the process proceeds to S824. On the other hand, if it is determined that measurement was not conducted (NO in S822), the process ends.

In step S824, correlation calculation portion 306 reads from memory 14, all data Iw of whole-body impedance Zw and data If of both-feet impedance Zf in the same time zone.

In succession, correlation calculation portion 306 calculates such correlation coefficients cf, df as satisfying the following correlation equation, based on whole-body impedance Zw and both-feet impedance Zf measured in steps S106 and S112 respectively and on whole-body impedance Zw and impedance Zf read in step S824 (S826).

$$Zw = cf*Zf + df$$

The second correlation information setting processing thus ends.

As the first and second correlation information setting processing as above is performed in the third embodiment, correlation coefficients ch, dh are stored as correlation information Rwh and correlation coefficients cf, df are stored as correlation information Rwf in step S118. Moreover, body fat rate % FAT_w % calculated in step S108 is stored as body fat rate data F. Further, impedances Zw, Zh, and Zf calculated in steps S106, S110, and S112 are stored as data Iw, Ih, and If respectively.

Figure 25:
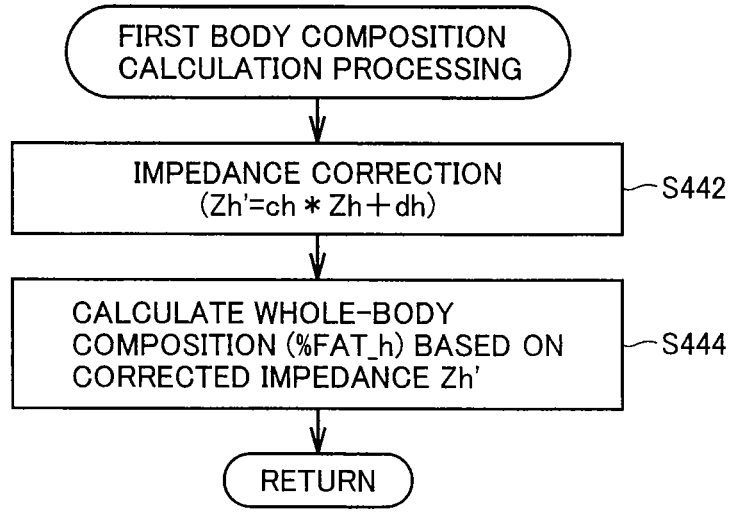
FIG. 25 is a flowchart showing first body composition calculation processing in the third embodiment of the present invention.

In the first body composition calculation processing in the third embodiment of the present invention shown in FIG. 25, it is assumed that immediately preceding correlation coefficients ch, dh in the same time zone have been read in step S308.

Referring to FIG. 25, correction portion 304 corrects both-hand impedance Zh measured in step S306 based on correlation coefficients ch, dh read as the correlation information in step S308 (step S442). More specifically, corrected impedance Zh' is calculated with the following equation.

$$Zh' = ch*Zh + dh$$

Thereafter, second body composition calculation portion 105 calculates the whole-body composition (% FAT_h) based on corrected impedance Zh' (step S444). More specifically, the body fat rate is calculated based on corrected impedance Zh', the body information of the subject, and equations (1) and (2) above (substituting the value of "Zh'" into "Zw" in estimation equation (2)).

As the processing above is performed, body fat rate % FAT_h calculated in step S444 is stored in memory 14 as whole-body composition data F in step S312, and presented to the subject in step S314.

Figure 26:
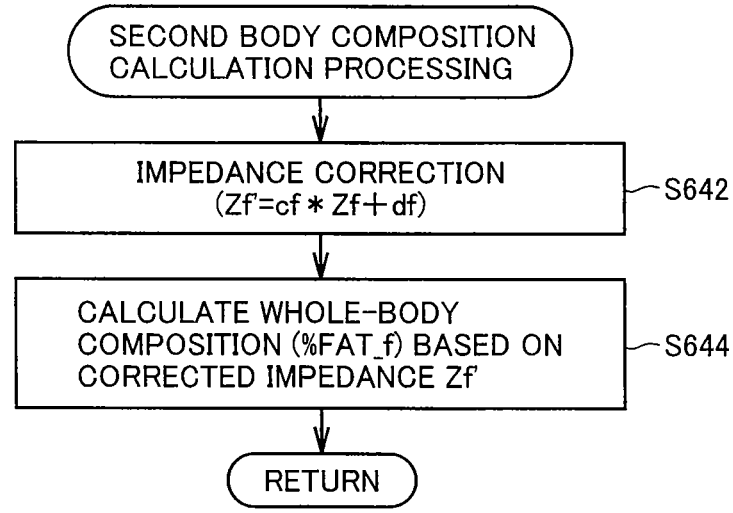
FIG. 26 is a flowchart showing second body composition calculation processing in the third embodiment of the present invention.

In the second body composition calculation processing in the third embodiment of the present invention shown in FIG. 26, it is assumed that immediately preceding correlation coefficients cf, df in the same time zone have been read in step S508.

Referring to FIG. 26, correction portion 304 corrects both-feet impedance Zf measured in step S506 based on correlation coefficients cf, df read as the correlation information in step S508 (step S642). More specifically, corrected impedance Zf' is calculated with the following equation.

$$Zf' = cf*Zf + df$$

Thereafter, second body composition calculation portion 105 calculates the whole-body composition (% FAT_f) based on corrected impedance Zf' (step S644). More specifically, the body fat rate is calculated based on corrected impedance Zf', the body information of the subject, and equations (1) and (2) above (substituting the value of "Zr" into "Zw" in estimation equation (2)).

As the processing above is performed, body fat rate % FAT_f calculated in step S644 is stored in memory 14 as whole-body composition data F in step S512, and presented to the subject in step S514.

As described above, in the third embodiment of the present invention, in the whole-body measurement mode, correlation between the whole-body impedance and the two-limb impedance is set as the correlation information. Then, in the simplified measurement mode as well, highly reliable whole-body composition corresponding to the subject can be calculated.

In the present embodiment, data Iw of the whole-body impedance and data Ih, If of the two-limb impedance stored in the storage area for the same time zone are all read in steps S804 and S824, however, for example, data within a prescribed period in the past may be read. Alternatively, record Rb may further include all impedance data Iw, Ih, and If within a prescribed period. Then, immediately preceding data in the same time zone should only be read.

In addition, in the present embodiment, correlation between the whole-body impedance and the two-limb impedance is set as the correlation information, however, correlation between the potential difference of the whole-body and the potential difference between the two limbs may be set as the correlation information.

Description of body composition monitor 100 according to the first to third embodiments above is given assuming that the body fat rate is calculated as the whole-body composition, however, instead of or in addition to the body fat rate, other biological information such as muscle rate may be calculated.

The method of measuring body composition performed by the body composition monitor according to the present invention may also be provided as a program. Such a program can be recorded on an optical medium such as a CD-ROM (Compact Disk-ROM) or a computer-readable recording medium such as a memory card, and can be provided as a program product. Alternatively, the program may be provided by downloading through the network.

The provided program product is installed in a program storage unit such as a hard disk for execution. It is noted that the program product includes the program itself and the recording medium recording the program.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

The invention claimed is:

1. A body composition monitor for measuring whole-body composition of a subject, comprising:
a plurality of hand electrodes and a plurality of foot electrodes;
a detection portion for detecting a first potential difference between a hand and a foot by applying a current across the hand and the foot of said subject through both of said hand electrode and said foot electrode and detecting a second potential difference between both hands or between both feet by applying a current across said both hands or across said both feet of said subject through any one of said hand electrodes and said foot electrodes; and
a controller configured to
calculate first whole-body composition using whole-body impedance based on a result of detection of said first potential difference,
correct two-limb impedance based on a result of detection of said second potential difference,
calculate second whole-body composition using the corrected two-limb impedance,
calculate a third whole-body composition of said subject based on said two-limb impedance based on said second potential difference detected in detection of said first potential difference, body information of said subject, and a prescribed second estimation equation showing a relation among said two-limb impedance, said body information and said whole-body composition, and
calculate a correction value for said two-limb impedance that said first whole-body composition is equal to said third whole-body composition;
store data of said correction value as correlation information in a storage portion,
determine whether a differential value between said first whole-body composition and said third whole-body composition is equal to or smaller than a prescribed threshold value,
calculate said first whole-body composition of said subject based on said whole-body impedance, the body information of said subject, and a prescribed first estimation equation showing a relation among said whole-body impedance, said body information and said whole-body composition, and
calculate said correction value based on a determination that said differential value exceeds said threshold value.

2. The body composition monitor according to claim 1, wherein
the controller is further configured to correct said two-limb impedance based on the data of said correction value, and
calculate said second whole-body composition of said subject based on corrected said two-limb impedance, said body information of said subject, and said second estimation equation.

3. The body composition monitor according to claim 2, further comprising a time keeping portion for keeping time; and wherein the controller is further configured to determine a time zone based on data output from said time keeping portion, said storage portion stores the data of said correction value in association with the time zone in which said detection portion detects said first potential difference.

4. The body composition monitor according to claim 2, further comprising a time keeping portion for keeping time, wherein
said storage portion stores the data of said correction value in association with a time in which said first potential difference is detected.

5. The body composition monitor according to claim 3, wherein
the controller is further configured to correct said two-limb impedance based on the data of said correction value corresponding to the time zone in which said detection portion detects said second potential difference.

6. A body composition monitor, comprising:
a plurality of hand electrodes and a plurality of foot electrodes;
a detection portion for detecting a first potential difference between a hand and a foot by applying a current across the hand and the foot of said subject through both of said hand electrode and said foot electrode and detecting a second potential difference between both hands or between both feet by applying a current across said both hands or across said both feet of said subject through any one of said hand electrodes and said foot electrodes; and a controller configured to calculate first whole-body composition using whole-body impedance based on a result of detection of said first potential difference;

correct two-limb impedance based on a result of detection of said second potential difference;

calculate second whole-body composition using said two-limb impedance corrected by said correction portion, calculate a third whole-body composition of said subject based on said two-limb impedance based on said second potential difference detected in detection of said first potential difference, body information of said subject, and a prescribed second estimation equation showing a relation among said two-limb impedance, said body information and said whole-body composition, calculate a correction value for said two-limb impedance that said first whole-body composition is equal to said third whole-body composition, store data of said correction value as correlation information in a storage portion, and determine whether a differential value between said first whole-body composition and said third whole-body composition is equal to or smaller than a prescribed threshold value, calculate said first whole-body composition of said subject based on said whole-body impedance, the body information of said subject, and a prescribed estimation equation showing relation among said whole-body impedance, said body information and said whole-body composition, calculate said correction value based on a determination that said differential value exceeds said threshold value, and calculate a correlation between said whole-body impedance and said two-limb impedance based on said second potential difference detected in detection of said first potential difference.

7. The body composition monitor according to claim 6, wherein the controller is further configured to correct said two-limb impedance based on said correlation data, and calculate said second whole-body composition based on corrected said two-limb impedance, said body information of said subject, and said estimation equation.

8. The body composition monitor according to claim 7, further comprising a time keeping portion for keeping time; and wherein the controller is further configured to determine a time zone based on data output from said time keeping portion, and said storage portion stores said correlation data in association with the time zone in which said detection portion detects said first potential difference.

9. The body composition monitor according to claim 7, further comprising a time keeping portion for keeping time, wherein said storage portion stores said correlation data in association with a time in which said first potential difference is detected.

10. The body composition monitor according to claim 8, wherein the controller is further configured to correct said two-limb impedance based on said correlation data corresponding to the time zone in which said second potential difference is detected.

11. The body composition monitor according to claim 1 or 6, wherein the controller is further configured to select execution of processing for first body composition calculation or processing for second body composition calculation.

12. The body composition monitor according to claim 11, wherein the controller is further configured to sense a state of contact of said hand electrode and said foot electrode with a body of said subject, and select execution of processing for first body composition calculation when contact of both of said hand electrode and said foot electrode with said body is sensed and select execution of processing for second body composition calculation when contact of said hand electrode or said foot electrode with said body is sensed.

13. The body composition monitor according to claim 11, further comprising:

a first unit provided with said hand electrode, and the controller, that can be gripped with said both hands of said subject;

a second unit provided with said foot electrode, on which said both feet of said subject can be placed; and a cable for establishing electrical connection between said first unit and said second unit, said cable being attachable/detachable to/from said first unit or said second unit, wherein the controller is further configured to sense whether said cable is connected to said first unit or said second unit, and select execution of processing for first body composition calculation when connection is sensed and select execution of processing for second body composition calculation for said both hands when absence of connection is sensed.

14. The body composition monitor according to claim 6, further comprising:

a first unit provided with said hand electrode, that can be gripped with said both hands of said subject;

a second unit provided with said foot electrode, on which said both feet of said subject can be placed, said second unit including a housing portion for housing said first unit and a housing sensing portion for sensing whether said first unit is housed in said housing portion; and a cable for establishing electrical connection between said first unit and said second unit, wherein the controller is further configured to select execution of said second body composition calculation when said housing sensing portion senses housing and selects execution of processing for first body composition calculation for said both feet when said housing sensing portion senses absence of housing.

15. The body composition monitor according to claim 6, the controller is further configured to determine whether said storage portion has stored said correlation information when execution of said second body composition calculation is selected; and give notification to urge said subject of use in a mode corresponding to execution of the processing for first body composition calculation when it is determined that said correlation information has not been stored.

16. The body composition monitor according to claim 6, the controller is further configured to determine whether said storage portion has stored said correlation information when execution of the processing for second body composition calculation; and notify said subject of prohibition of use in a mode corresponding to execution of the processing for second body composition calculation when it is determined that said correlation information has not been stored.

17. The body composition monitor according to claim 6, further comprising a time keeping portion for keeping time and day, said correlation information being stored in said storage portion in association with time and day when said correlation information was set;
wherein the controller is further configured to determine whether a prescribed time period has elapsed since said time and day stored in said storage portion, when execution of the processing for second body composition calculation portion is selected; and
notify said subject of prohibition of use in a mode corresponding to execution of the processing for second body composition calculation when it is determined that said time period has elapsed.

18. The body composition monitor according to claim 6, the controller is further configured to determine whether said storage portion has stored said correlation information when execution of said second body composition calculation is selected; and
notify that correction processing is not applicable in presenting calculated said second whole-body composition to said subject, when it is determined that said correlation information has not been stored.

19. The body composition monitor according to claim 1 or 6, further comprising:
a first unit provided with said hand electrode, that can be gripped with said both hands of said subject;
a second unit provided with said foot electrode, on which said both feet of said subject can be placed, said second unit including a weight measurement portion for measuring weight out of said body information; and
a weight storage portion for storing said weight measured by said weight measurement portion, wherein
the controller is further configured to calculate said second whole-body composition of said subject by reading said weight stored in said weight storage portion.

20. A body composition monitor for measuring whole-body composition of a subject, comprising:
a plurality of hand electrodes and a plurality of foot electrodes;
a detection portion for detecting a first potential difference between a hand and a foot by applying a current across the hand and the foot of said subject through both of said hand electrode and said foot electrode and detecting a second potential difference between both hands or between both feet by applying a current across said both hands or across both said feet of said subject through any one of said hand electrodes and said foot electrodes;
a time keeping portion for keeping time; and
a controller configured to
calculate first whole-body composition using whole-body impedance based on a result of detection of said first potential difference;
calculate second whole-body composition using two-limb impedance based on a result of detection of said second potential difference;
correct calculated said second whole-body composition based on correlation information representing relation between said first whole-body composition and said second whole-body composition;
determine a time zone of a day based on data output from said time keeping portion,
calculate correlation between said first whole-body composition and said second whole-body composition based on said second potential difference detected in detection of said first potential difference, and
a storage portion for storing correlation data representing said correlation as said correlation information, wherein
said storage portion stores said correlation data in association with the time zone in which said first potential difference is detected,
said correlation information is stored in said storage portion in association with time and day when said correlation information was set,
the controller is further configured to determine whether a prescribed time period has elapsed since said time and day stored in said storage portion, when execution of processing for second body composition calculation portion is selected, and
notify said subject of prohibition of use in a mode corresponding to execution of the processing for second body composition calculation when it is determined that said time period has elapsed.

21. The body composition monitor according to claim 20, wherein
the controller is further configured to calculate said first whole-body composition of said subject based on said whole-body impedance, body information of said subject, and a prescribed first estimation equation showing relation among said whole-body impedance, said body information and said whole-body composition,
the controller is further configured to calculate said second whole-body composition of said subject based on said two-limb impedance, said body information of said subject, and a prescribed second estimation equation showing relation among said two-limb impedance, said body information and said whole-body composition.

22. The body composition monitor according to claim 21, wherein
the controller is further configured to correct said second whole-body composition based on said correlation data corresponding to the time zone in which said second potential difference is detected.

23. The body composition monitor according to claim 21, the controller is further configured to select execution of processing for first body composition calculation or processing for second body composition calculation.

24. The body composition monitor according to claim 23, wherein
the controller is further configured to sense a state of contact of said hand electrode and said foot electrode with a body of said subject, and
select execution of processing for first body composition calculation when contact of both of said hand electrode and said foot electrode with said body is sensed and select execution of processing for second body composition calculation when contact of said hand electrode or said foot electrode with said body is sensed.

25. The body composition monitor according to claim 23, further comprising:
a first unit provided with said hand electrode, said storage portion, and the controller, that can be gripped with said both hands of said subject;
a second unit provided with said foot electrode, on which said both feet of said subject can be placed; and
a cable for establishing electrical connection between said first unit and said second unit, said cable being attachable/detachable to/from said first unit or said second unit, wherein the controller is further configured to sense whether said cable is connected to said first unit or said second unit, and select execution of processing for first body composition calculation when connection is sensed and select execution of processing for second body composition calculation for said both hands when absence of connection is sensed.

26. The body composition monitor according to claim 23, further comprising:

a first unit provided with said hand electrode, that can be gripped with said both hands of said subject;

a second unit provided with said foot electrode, on which said both feet of said subject can be placed, said second unit including a housing portion for housing said first unit and a housing sensing portion for sensing whether said first unit is housed in said housing portion; and a cable for establishing electrical connection between said first unit and said second unit, wherein the controller is further configured to select execution of said second body composition calculation when said housing sensing portion senses housing and select execution of processing for first body composition calculation for said both feet when said housing sensing portion senses absence of housing.

27. The body composition monitor according to claim 23, the controller is further configured to determine whether said storage portion has stored said correlation information when execution of said second body composition calculation is selected; and give notification to urge said subject of use in a mode corresponding to execution of the processing for first body composition calculation when it is determined that said correlation information has not been stored.

28. The body composition monitor according to claim 23, the controller is further configured to determine whether said storage portion has stored said correlation information when execution of the processing for second body composition calculation is selected; and notify said subject of prohibition of use in a mode corresponding to execution of the processing for second body composition calculation when it is determined that said correlation information has not been stored.

29. The body composition monitor according to claim 23, wherein the controller is further configured to determine whether said storage portion has stored said correlation information when execution of said second body composition calculation is selected; and notify that correction processing is not applicable in presenting calculated said second whole-body composition to said subject, when it is determined that said correlation information has not been stored.

30. The body composition monitor according to claim 21, further comprising:

a first unit provided with said hand electrode, that can be gripped with said both hands of said subject;

a second unit provided with said foot electrode, on which said both feet of said subject can be placed, said second unit including a weight measurement portion for measuring weight out of said body information; and a weight storage portion for storing said weight measured by said weight measurement portion, wherein the controller is further configured to calculate said second whole-body composition of said subject by reading said weight stored in said weight storage portion.

31. A body composition monitor for measuring whole-body composition of a subject, comprising:

a plurality of hand electrodes and a plurality of foot electrodes;

a detection portion for detecting a first potential difference between a hand and a foot by applying a current across the hand and the foot of said subject through both of said hand electrode and said foot electrode and detecting a second potential difference between both hands or between both feet by applying a current across said both hands or across both said feet of said subject through any one of said hand electrodes and said foot electrodes;

a time keeping portion for keeping time;

a storage portion for storing data; and a controller configured to calculate first whole-body composition using whole-body impedance based on a result of detection of said first potential difference;

calculate second whole-body composition using two-limb impedance based on a result of detection of said second potential difference;

correct calculated said second whole-body composition based on correlation information representing relation between said first whole-body composition and said second whole-body composition;

determine a time zone of a day based on data output from said time keeping portion, calculate correlation between said first whole-body composition and said second whole-body composition based on said second potential difference detected in detection of said first potential difference, and store correlation data representing said correlation as said correlation information in association with a time in which said first potential difference is detected, said correlation information is stored in said storage portion in association with time and day when said correlation information was set, the controller is further configured to determine whether a prescribed time period has elapsed since said time and day stored in said storage portion, when execution of processing for second body composition calculation portion is selected, and notify said subject of prohibition of use in a mode corresponding to execution of the processing for second body composition calculation when it is determined that said time period has elapsed.

* * * * *